(12) United States Patent
Reiter

(10) Patent No.: US 6,197,810 B1
(45) Date of Patent: Mar. 6, 2001

(54) 3-(ARYLSULFONYLAMINO)-TETRAHYDROPYRAN-3-CARBOXYLIC ACID HYDROXAMIDES

(75) Inventor: Lawrence A. Reiter, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/579,059

(22) Filed: May 26, 2000

Related U.S. Application Data
(60) Provisional application No. 60/136,530, filed on May 28, 1999.

(51) Int. Cl.$^7$ .................................................. A01N 43/16
(52) U.S. Cl. ............................ 514/459; 549/419; 549/424
(58) Field of Search .................... 549/419, 424; 514/459

(56) References Cited

FOREIGN PATENT DOCUMENTS

| 606046 | 7/1994 | (EP) | ............... | C07D/213/42 |
| 9833768 | 8/1998 | (WO) | ............... | C07C/311/29 |

Primary Examiner—Bernard Dentz

(74) Attorney, Agent, or Firm—Peter C. Richardson; Paul H. Ginsburg; Garth Butterfield

(57) ABSTRACT

A compound of the formula

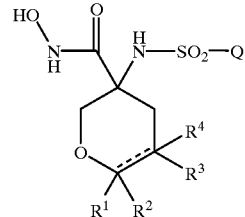

I wherein $R^1$, $R^2$, $R^3$, $R^4$ and Q are as defined above, are useful in the treatment of arthritis (including osteoarthritis and rheumatoid arthritis), cancer and other diseases. In addition, the compounds of the present invention may be used in combination therapy with standard non-steroidal anti-inflammatory drugs (NSAID's), COX-2 inhibitors and analgesics, and in combination with cytotoxic drugs such as adriamycin, daunomycin, cis-platinum, etoposide, taxol, taxotere and other alkaloids, such as vincristine, in the treatment of cancer.

30 Claims, No Drawings

3-(ARYLSULFONYLAMINO)-TETRAHYDROPYRAN-3-CARBOXYLIC ACID HYDROXAMIDES

This application claims benefit of Provisional Application 60/136,530 filed May 28, 1999.

BACKGROUND OF THE INVENTION

The present invention relates to 3-(arylsulfonylamino)-tetrahydropyran-3-carboxylic acid hydroxamide derivatives, and to pharmaceutical compositions and methods of treatment of inflammation, cancer as well as other disorders.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty-three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and autoimmune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopathology*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

It is recognized that different combinations of MMP's and ADAM's are expressed in different pathological situations. As such inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

Matrix metalloproteinase and reprolysin inhibitors are well known in the literature. Specifically, European Patent Publication 606,046, published Jul. 13, 1994, refers to certain heterocyclic MMP inhibitors. U.S. Pat. No. 5,861, 510, issued Jan. 19, 1999, refers to cyclic arylsulfonylamino hydroxamic acids that are useful as MMP inhibitors. PCT Publication WO 98/34918, published Aug. 13, 1998, refers to heterocyclic hydroxamic acids including certain dialkyl substituted compounds that are useful as MMP inhibitors. PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998 refers to phosphinates with MMP activity. PCT publication 98/33768, published Aug. 6, 1998, refers to N-unsubstituted arylsulfonylamino hydroxamic acids. PCT Publication WO 98/08825, published Mar. 5, 1998, refers to certain MMP inhibitors. Each of the above referenced publications and applications is hereby incorporated by reference in its entirety.

SUMMARY OF THE INVENTION

The present invention relates to a compound of the formula

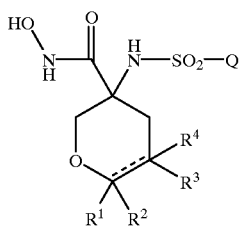

I wherein the dotted line represents an optional double bond, $R^1$, $R^2$, $R^3$, $R^4$ are each independently selected from the group consisting of hydrogen, hydroxy-, $(C_1-C_6)$alkyl-, $(C_1-C_6)$alkoxy-, $(C_1-C_6)$alkoxy$(C_1-C_6)$alkoxy-, $((C_1-C_6)$ alkyl)$_2$amino(C$_1$–C$_6$)alkoxy-, (C$_1$–C$_6$)alkylthio-, (C$_6$–C$_{10}$) aryl(C$_1$–C$_6$)alkoxy-, (C$_2$–C$_9$)heteroaryl(C$_1$–C$_6$)alkoxy-, (C$_6$–C$_{10}$)aryl(C$_1$–C$_6$)alkythio-, (C$_2$–C$_9$)heteroaryl(C$_1$–C$_6$) alkythio-, hydroxy(C$_1$–C$_6$)alkyl-, (C$_6$–C$_{10}$)aryl(C$_1$–C$_6$) alkyl-, (C$_2$–C$_9$)heteroaryl(C$_1$–C$_6$)alkyl-, (C$_1$–C$_6$)alkoxy (C$_1$–C$_6$)alkyl-, (C$_6$–C$_{10}$)aryl(C$_1$–C$_6$)alkoxy(C$_1$–C$_6$)alkyl-, (C$_2$–C$_9$)heteroaryl(C$_1$–C$_6$)alkoxy(C$_1$–C$_6$)alkyl-, (C$_1$–C$_6$) alkylamino(C$_1$–C$_6$)alkyl-, ((C$_1$–C$_6$)alkyl)$_2$amino(C$_1$–C$_6$) alkyl-, [(C$_6$–C$_{10}$)aryl(C$_1$–C$_6$)alkyl]amino(C$_1$–C$_6$)alkyl-, [(C$_6$–C$_{10}$)aryl(C$_1$–C$_6$)alkyl]((C$_1$–C$_6$)alkyl)amino(C$_1$–C$_6$) alkyl-, (C$_6$–C$_{10}$)aryl, [(C$_2$–C$_9$)heteroaryl(C$_1$–C$_6$)alkyl] amino(C$_1$–C$_6$)alkyl-, (C$_2$–C$_9$)heteroaryl and [(C$_2$–C$_9$) heteroaryl(C$_1$–C$_6$)alkyl]((C$_1$–C$_6$)alkyl)amino(C$_1$–C$_6$)alkyl-; wherein each of said (C$_6$–C$_{10}$)aryl or (C$_2$–C$_9$)heteroaryl moieties of said (C$_6$–C$_{10}$)aryl(C$_1$–C$_6$)alkoxy-, (C$_2$–C$_9$) heteroaryl(C$_1$–C$_6$)alkoxy-, (C$_6$–C$_{10}$)aryl(C$_1$–C$_6$)alkylthio-, (C$_2$–C$_9$)heteroaryl(C$_1$–C$_6$)alkythio-, (C$_6$–C$_{10}$)aryl(C$_1$–C$_6$) alkyl-, (C$_2$–C$_9$)heteroaryl(C$_1$–C$_6$)alkyl-, (C$_6$–C$_{10}$)aryl (C$_1$–C$_6$)alkoxy(C$_1$–C$_6$)alkyl-, (C$_2$–C$_9$)heteroaryl(C$_1$–C$_6$) alkoxy(C$_1$–C$_6$)alkyl-, [(C$_6$–C$_{10}$)aryl(C$_1$–C$_6$)alkyl]amino (C$_1$–C$_6$)alkyl-, [(C$_6$–C$_{10}$)aryl(C$_1$–C$_6$)alkyl]((C$_1$–C$_6$)alkyl) amino(C$_1$–C$_6$)alkyl-, (C$_6$–C$_{10}$)aryl, [(C$_2$–C$_9$)heteroaryl (C$_1$–C$_6$)alkyl]amino(C$_1$–C$_6$)alkyl-, (C$_2$–C$_9$)heteroaryl and [(C$_2$–C$_9$)heteroaryl(C$_1$–C$_6$)alkyl]((C$_1$–C$_6$)alkyl)amino (C$_1$–C$_6$)alkyl- are optionally substituted on any of the ring carbon atoms capable of forming an additional bond by one or more substituents per ring, most preferably one to three substituents on the terminal ring (i.e. the ring furthest from the point of attachment), independently selected from fluoro, chloro, cyano, nitro, trifluoromethyl, (C$_1$–C$_6$)alkoxy, (C$_6$–C$_{10}$)aryloxy, trifluoromethoxy, difluoromethoxy, or (C$_1$–C$_6$)alkyl;

or R$^1$ can be taken together with R$^2$ to form a carbonyl group;

or R$^3$ can be taken together with R$^4$ to form a carbonyl group;

Q is (C$_1$–C$_6$)alkyl, (C$_6$–C$_{10}$)aryl, (C$_2$–C$_9$)heteroaryl, (C$_6$–C$_{10}$)aryloxy(C$_1$–C$_6$)alkyl, (C$_6$–C$_{10}$)aryloxy(C$_6$–C$_{10}$) aryl, (C$_6$–C$_{10}$)aryloxy(C$_2$–C$_9$)heteroaryl, (C$_6$–C$_{10}$)aryl (C$_1$–C$_6$)alkyl, (C$_6$–C$_{10}$)aryl(C$_6$–C$_{10}$)aryl, (C$_6$–C$_{10}$)aryl (C$_2$–C$_9$)heteroaryl, (C$_6$–C$_{10}$)aryl(C$_6$–C$_{10}$)aryl(C$_1$–C$_6$)alkyl, (C$_6$–C$_{10}$)aryl(C$_6$–C$_{10}$)aryl(C$_6$–C$_{10}$)aryl, (C$_6$–C$_{10}$)aryl (C$_6$–C$_{10}$)aryl(C$_2$–C$_9$)heteroaryl, (C$_2$–C$_9$)heteroaryl(C$_1$–C$_6$) alkyl, (C$_2$–C$_9$)heteroaryl(C$_6$–C$_{10}$)aryl, (C$_2$–C$_9$)heteroaryl (C$_2$–C$_9$)heteroaryl, (C$_6$–C$_{10}$)aryl(C$_1$–C$_6$)alkoxy(C$_1$–C$_6$) alkyl, (C$_6$–C$_{10}$)aryl(C$_1$–C$_6$)alkoxy(C$_6$–C$_{10}$)aryl, (C$_6$–C$_{10}$) aryl(C$_1$–C$_6$)alkoxy(C$_2$–C$_9$)heteroaryl, (C$_2$–C$_9$) heteroaryloxy(C$_1$–C$_6$)alkyl, (C$_2$–C$_9$)heteroaryloxy(C$_6$–C$_{10}$) aryl, (C$_2$–C$_9$)heteroaryloxy(C$_2$–C$_9$)heteroaryl, (C$_2$–C$_9$) heteroaryl(C$_1$–C$_6$)alkoxy(C$_1$–C$_6$)alkyl, (C$_2$–C$_9$)heteroaryl (C$_1$–C$_6$)alkoxy(C$_6$–C$_{10}$)aryl or (C$_2$–C$_9$)heteroaryl(C$_1$–C$_6$) alkoxy(C$_2$–C$_9$)heteroaryl;

wherein each (C$_6$–C$_{10}$)aryl or (C$_2$–C$_9$)heteroaryl moieties of said (C$_6$–C$_{10}$)aryl, (C$_2$–C$_9$)heteroaryl, (C$_6$–C$_{10}$)aryloxy (C$_1$–C$_6$)alkyl, (C$_6$–C$_{10}$)aryloxy(C$_6$–C$_{10}$)aryl, (C$_6$–C$_{10}$) aryloxy(C$_2$–C$_9$)heteroaryl, (C$_6$–C$_{10}$)aryl(C$_1$–C$_6$)alkyl, (C$_6$–C$_{10}$)aryl(C$_6$–C$_{10}$)aryl, (C$_6$–C$_{10}$)aryl(C$_2$–C$_9$)heteroaryl, (C$_6$–C$_{10}$)aryl(C$_6$–C$_{10}$)aryl(C$_1$–C$_6$)alkyl, (C$_6$–C$_{10}$)aryl (C$_6$–C$_{10}$)aryl(C$_6$–C$_{10}$)aryl, (C$_6$–C$_{10}$)aryl(C$_6$–C$_{10}$)aryl (C$_2$–C$_9$)heteroaryl, (C$_2$–C$_9$)heteroaryl(C$_1$–C$_6$)alkyl, (C$_2$–C$_9$)heteroaryl(C$_6$–C$_{10}$)aryl, (C$_2$–C$_9$)heteroaryl(C$_2$–C$_9$) heteroaryl, (C$_6$–C$_{10}$)aryl(C$_1$–C$_6$)alkoxy(C$_1$–C$_6$)alkyl, (C$_6$–C$_{10}$)aryl(C$_1$–C$_6$)alkoxy(C$_6$–C$_{10}$)aryl, (C$_6$–C$_{10}$)aryl (C$_1$–C$_6$)alkoxy(C$_2$–C$_9$)heteroaryl, (C$_2$–C$_9$)heteroaryloxy (C$_1$–C$_6$)alkyl, (C$_2$–C$_9$)heteroaryloxy(C$_6$–C$_{10}$)aryl, (C$_2$–C$_9$) heteroaryloxy(C$_2$–C$_9$)heteroaryl, (C$_2$–C$_9$)heteroaryl(C$_1$–C$_6$) alkoxy(C$_1$–C$_6$)alkyl, (C$_2$–C$_9$)heteroaryl(C$_1$–C$_6$)alkoxy (C$_6$–C$_{10}$)aryl or (C$_2$–C$_9$)heteroaryl(C$_1$–C$_6$)alkoxy(C$_2$–C$_9$) heteroaryl is optionally substituted on any of the ring carbon atoms capable of forming an additional bond by one or more substituents per ring, most preferably one to three substituents on the terminal ring (i.e. the ring furthest from the point of attachment), independently selected from fluoro, chloro, bromo, (C$_1$–C$_6$)alkyl, (C$_1$–C$_6$)alkoxy, perfluoro(C$_1$–C$_3$) alkyl (preferably trifluoromethyl), perfluoro(C$_1$–C$_3$)alkoxy (preferably trifluoromethoxy or difluoromethoxy) and (C$_6$–C$_{10}$)aryloxy;

with the proviso that when the dotted line is a double bond then one of R$^1$ or R$^2$ and one of R$^3$ or R$^4$ is absent;

with the proviso that when one of R$^1$ or R$^2$ is hydroxy then the other of R$^1$ or R$^2$ cannot be hydroxy, (C$_1$–C$_6$)alkoxy, (C$_1$–C$_6$)alkoxy(C$_1$–C$_6$)alkoxy-, ((C$_1$–C$_6$)alkyl)$_2$amino (C$_1$–C$_6$)alkoxy-, (C$_1$–C$_6$)alkylthio-, (C$_6$–C$_{10}$)aryl(C$_1$–C$_6$) alkoxy-, (C$_2$–C$_9$)heteroaryl(C$_1$–C$_6$)alkoxy-, (C$_6$–C$_{10}$)aryl (C$_1$–C$_6$)alkythio, or (C$_2$–C$_9$)heteroaryl(C$_1$–C$_6$)alkythio-; and with the proviso that when one of R$^3$ or R$^4$ is hydroxy then the other of R$^3$ or R$^4$ cannot be hydroxy, (C$_1$–C$_6$)alkoxy-, (C$_1$–C$_6$)alkoxy(C$_1$–C$_6$)alkoxy-, ((C$_1$–C$_6$)alkyl)$_2$amino (C$_1$–C$_6$)alkoxy-, (C$_1$–C$_6$)alkylthio, (C$_6$–C$_{10}$)aryl(C$_1$–C$_6$) alkoxy-, (C$_2$–C$_9$)heteroaryl(C$_1$–C$_6$)alkoxy-, (C$_6$–C$_{10}$)aryl (C$_1$–C$_6$)alkythio-, or (C$_2$–C$_9$)heteroaryl(C$_1$–C$_6$)alkythio-;

or the pharmaceutically acceptable salts thereof.

The compounds of formula I contain chiral centers and therefore exist in different enantiomeric forms. This invention relates to all optical isomers, tautomers, enantiomers, diasteriomers and stereoisomers of the compounds of formula I and mixtures thereof. One set of preferred isomers include the following which includes both of its stereoisomers I' (derived from L-serine starting materials) and I" (derived from D-serine starting materials):

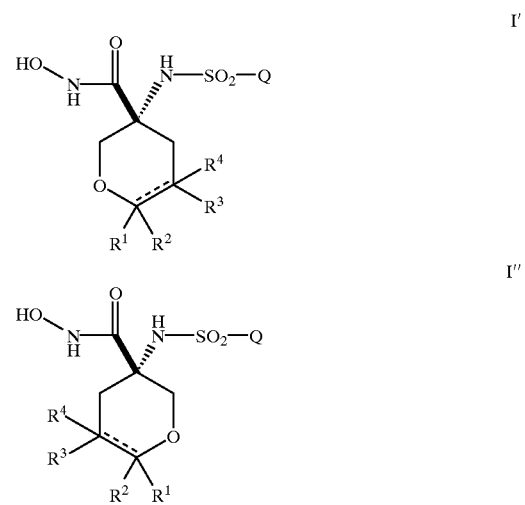

The term "alkyl", as used herein, unless otherwise indicated, includes saturated monovalent hydrocarbon radicals having straight, branched or cyclic moieties or combinations thereof optionally substituted by one to three suitable substituents as defined below.

The term "alkoxy", as used herein, includes O-alkyl groups wherein "alkyl" is defined above optionally substituted by one to three suitable substituents as defined below.

The term "[(C$_6$–C$_{10}$)aryl(C$_1$–C$_6$)alkyl]amino(C$_1$–C$_6$) alkyl-", as used herein, refers to a group of the formula

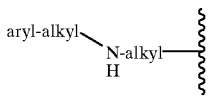

The term "[$(C_6-C_{10})$aryl$(C_1-C_6)$alkyl]$((C_1-C_6)$alkyl) amino$(C_1-C_6)$alkyl-", as used herein, refers to a group of the formula

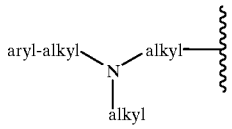

The term "[$(C_2-C_9)$heteroaryl$(C_1-C_6)$alkyl]amino $(C_1-C_6)$alkyl-", as used herein, refers to a group of the formula

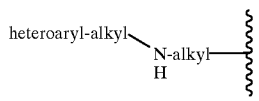

The term "[$(C_2-C_9)$heteroaryl$(C_1-C_6)$alkyl]$((C_1-C_6)$ alkyl)amino$(C_1-C_6)$alkyl-", as used herein, refers to a group of the formula

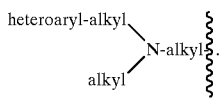

The term "aryl", as used herein, unless otherwise indicated, includes an organic radical derived from an aromatic hydrocarbon by removal of one hydrogen, such as phenyl or naphthyl, optionally substituted by 1 to 3 suitable substituents such as fluoro, chloro, cyano, nitro, trifluoromethyl, $(C_1-C_6)$alkoxy, $(C_6-C_{10})$aryloxy, trifluoromethoxy, difluoromethoxy, or $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 3 suitable substituents as defined below, such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

Preferred compounds of formula I include those wherein Q is optionally substituted $(C_6-C_{10})$aryl, $(C_6-C_{10})$aryl$(C_6-C_{10})$aryl-, $(C_6-C_{10})$aryloxy$(C_6-C_{10})$aryl-, $(C_6-C_{10})$aryloxy$(C_2-C_9)$heteroaryl-, $(C_2-C_9)$heteroaryl-, $(C_2-C_9)$heteroaryl$(C_2-C_9)$heteroaryl-, $(C_6-C_{10})$aryl$(C_2-C_9)$heteroaryl-, $(C_2-C_9)$heteroaryl$(C_6-C_{10})$aryl-, $(C_2-C_9)$heteroaryloxy$(C_6-C_{10})$aryl-, $(C_6-C_{10})$aryl$(C_1-C_6)$alkoxy $(C_6-C_{10})$aryl-, or $(C_2-C_9)$heteroaryl$(C_1-C_6)$alkoxy $(C_6-C_{10})$aryl-.

Other preferred compounds of formula I include those wherein Q is optionally substituted $(C_6-C_{10})$aryloxy $(C_6-C_{10})$aryl- or $(C_6-C_{10})$aryl$(C_1-C_6)$alkoxy$(C_6-C_{10})$aryl-.

Other preferred compounds of formula I include those wherein $R^1$ or $R^2$ is $(C_1-C_6)$alkyl, hydroxy$(C_1-C_6)$alkyl-, $(C_6-C_{10})$aryl$(C_1-C_6)$alkyl-, $(C_2-C_9)$heteroaryl$(C_1-C_6)$ alkyl-, $(C_1-C_6)$alkoxy$(C_1-C_6)$alkyl-, $(C_6-C_{10})$aryl$(C_1-C_6)$ alkoxy$(C_1-C_6)$alkyl-, $(C_2-C_9)$heteroaryl$(C_1-C_6)$alkoxy $(C_1-C_6)$alkyl-, $(C_1-C_6)$alkylamino$(C_1-C_6)$alkyl-, $((C_1-C_6)$ alkyl$)_2$amino$(C_1-C_6)$alkyl-, [$(C_6-C_{10})$aryl$(C_1-C_6)$alkyl] amino$(C_1-C_6)$alkyl-, [$(C_6-C_{10})$aryl$(C_1-C_6)$alkyl]$((C_1-C_6)$ alkyl)amino$(C_1-C_6)$alkyl-, $(C_6-C_{10})$aryl, [$(C_2-C_9)$ heteroaryl$(C_1-C_6)$alkyl]amino$(C_1-C_6)$alkyl-, $(C_2-C_9)$ heteroaryl, or [$(C_2-C_9)$heteroaryl$(C_1-C_6)$alkyl]$((C_1-C_6)$ alkyl)amino$(C_1-C_6)$alkyl-.

A subclass of compounds of formula I of particular interest include those wherein $R^1$ or $R^2$ is $(C_1-C_6)$alkyl, hydroxy$(C_1-C_6)$alkyl-, $(C_6-C_{10})$aryl$(C_1-C_6)$alkyl-, $(C_2-C_9)$ heteroaryl$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$ heteroaryl$(C_1-C_6)$alkoxy$(C_1-C_6)$alkyl-, $(C_6-C_{10})$aryl or $(C_2-C_9)$heteroaryl.

Another subclass of compounds of formula I of particular interest include those wherein $R^1$ or $R^2$ is $(C_1-C_6)$alkyl, $(C_6-C_{10})$aryl$(C_1-C_6)$alkyl-, $(C_2-C_9)$heteroaryl$(C_1-C_6)$ alkyl-, $(C_6-C_{10})$aryl or $(C_2-C_9)$heteroaryl.

Another subclass of compounds of formula I of particular interest include those wherein $R^1$ or $R^2$ is $(C_1-C_6)$alkyl, $(C_6-C_{10})$aryl or $(C_2-C_9)$heteroaryl.

Another subclass of compounds of formula I of particular interest include those wherein $R^1$ or $R^2$ is hydroxy$(C_1-C_6)$ alkyl-, $(C_1-C_6)$alkoxy$(C_1-C_6)$alkyl-, $(C_6-C_{10})$aryl$(C_1-C_6)$ alkoxy$(C_1-C_6)$alkyl-, or $(C_2-C_9)$heteroaryl$(C_1-C_6)$alkoxy $(C_1-C_6)$alkyl-.

Another subclass of compounds of formula I of particular interest include those wherein $R^1$ or $R^2$ is $(C_1-C_6)$alkoxy $(C_1-C_6)$alkyl-.

Another subclass of compounds of formula I of particular interest include those wherein $R^1$ or $R^2$ is $(C_1-C_6)$alkoxy, $(C_1-C_6)$alkoxy$(C_1-C_6)$alkoxy-, $((C_1-C_6)$alkyl$)_2$amino $(C_1-C_6)$alkoxy-, $(C_1-C_6)$alkylthio, $(C_6-C_{10})$aryl$(C_1-C_6)$ alkoxy-, $(C_2-C_9)$heteroaryl$(C_1-C_6)$alkoxy-, $(C_6-C_{10})$aryl $(C_1-C_6)$alkythio-, or $(C_2-C_9)$heteroaryl$(C_1-C_6)$alkythio-.

Another subclass of compounds of formula I of particular interest include those wherein $R^1$ or $R^2$ is $(C_1-C_6)$alkoxy, $(C_1-C_6)$alkoxy$(C_1-C_6)$alkoxy-, $(C_6-C_{10})$aryl$(C_1-C_6)$ alkoxy-, or $(C_2-C_9)$heteroaryl$(C_1-C_6)$alkoxy-.

Another subclass of compounds of formula I of particular interest include those wherein $R^1$ or $R^2$ is $(C_1-C_6)$alkoxy or $(C_1-C_6)$alkoxy$(C_1-C_6)$alkoxy-.

Another subclass of compounds of formula I of particular interest include those wherein $R^3$ or $R^4$ is $(C_1-C_6)$alkyl, hydroxy($C_1$–$C_6$)alkyl-, ($C_6$–$C_{10}$)aryl($C_1$–$C_6$)alkyl-, ($C_2$–$C_9$) heteroaryl($C_1$–$C_6$)alkyl-, ($C_1$–$C_6$)alkoxy($C_1$–$C_6$)alkyl-, ($C_6$–$C_{10}$)aryl($C_1$–$C_6$)alkoxy($C_1$–$C_6$)alkyl-, ($C_2$–$C_9$) heteroaryl($C_1$–$C_6$)alkoxy($C_1$–$C_6$)alkyl-, ($C_1$–$C_6$)alkylamino ($C_1$–$C_6$)alkyl-, (($C_1$–$C_6$)alkyl)$_2$amino($C_1$–$C_6$)alkyl-, [($C_6$–$C_{10}$)aryl($C_1$–$C_6$)alkyl]amino($C_1$–$C_6$)alkyl-, ($C_6$–$C_{10}$) aryl, [($C_6$–$C_{10}$)aryl($C_{1-6}$)alkyl](($C_1$–$C_6$)alkyl)amino ($C_1$–$C_6$)alkyl-, ($C_2$–$C_9$)heteroaryl, [($C_2$–$C_9$)heteroaryl ($C_1$–$C_6$)alkyl]amino($C_1$–$C_6$)alkyl-, or [($C_2$–$C_9$)heteroaryl ($C_1$–$C_6$)alkyl](($C_1$–$C_6$)alkyl)amino($C_1$–$C_6$)alkyl-.

Another subclass of compounds of formula I of particular interest include those wherein $R^3$ or $R^4$ is ($C_1$–$C_6$)alkyl, hydroxy($C_1$–$C_6$)alkyl-, ($C_6$–$C_{10}$)aryl($C_1$–$C_6$)alkyl-, ($C_2$–$C_9$) heteroaryl($C_1$–$C_6$)alkyl-, ($C_1$–$C_6$)alkoxy($C_1$–$C_6$)alkyl-, ($C_6$–$C_{10}$)aryl($C_1$–$C_6$)alkoxy($C_1$–$C_6$)alkyl-, ($C_2$–$C_9$) heteroaryl($C_1$–$C_6$)alkoxy($C_1$–$C_6$)alkyl-, ($C_6$–$C_{10}$)aryl or ($C_2$–$C_9$)heteroaryl.

Another subclass of compounds of formula I of particular interest include those wherein $R^3$ or $R^4$ is ($C_1$–$C_6$)alkyl-, ($C_6$–$C_{10}$)aryl($C_1$–$C_6$)alkyl-, ($C_2$–$C_9$)heteroaryl($C_1$–$C_6$) alkyl-, ($C_6$–$C_{10}$)aryl or ($C_2$–$C_9$)heteroaryl.

Another subclass of compounds of formula I of particular interest include those wherein $R^3$ or $R^4$ is ($C_1$–$C_6$)alkyl, ($C_6$–$C_{10}$)aryl or ($C_2$–$C_9$)heteroaryl.

Another subclass of compounds of formula I of particular interest include those wherein $R^3$ or $R^4$ is hydroxy($C_1$–$C_6$) alkyl-, ($C_1$–$C_6$)alkoxy($C_1$–$C_6$)alkyl-, ($C_6$–$C_{10}$)aryl($C_1$–$C_6$) alkoxy($C_1$–$C_6$)alkyl-, or ($C_2$–$C_9$)heteroaryl($C_1$–$C_6$)alkoxy ($C_1$–$C_6$)alkyl-.

Another subclass of compounds of formula I of particular interest include those wherein $R^3$ or $R^4$ is ($C_1$–$C_6$)alkoxy ($C_1$–$C_6$)alkyl-.

Another subclass of compounds of formula I of particular interest include those wherein $R^3$ or $R^4$ is ($C_1$–$C_6$)alkoxy-, ($C_1$–$C_6$)alkoxy($C_1$–$C_6$)alkoxy-, (($C_1$–$C_6$)alkyl)$_2$amino ($C_1$–$C_6$)alkoxy-, ($C_1$–$C_6$)alkylthio-, ($C_6$–$C_{10}$)aryl($C_1$–$C_6$) alkoxy-, ($C_2$–$C_9$)heteroaryl($C_1$–$C_6$)alkoxy-, ($C_6$–$C_{10}$)aryl ($C_1$–$C_6$)alkythio, or ($C_2$–$C_9$)heteroaryl($C_1$–$C_6$)alkythio-.

Another subclass of compounds of formula I of particular interest include those wherein $R^3$ or $R^4$ is ($C_1$–$C_6$)alkoxy-, ($C_1$–$C_6$)alkoxy($C_1$–$C_6$)alkoxy-, ($C_6$–$C_{10}$)aryl($C_1$–$C_6$) alkoxy-, or ($C_2$–$C_9$)heteroaryl($C_1$–$C_6$)alkoxy-.

Another subclass of compounds of formula I of particular interest include those wherein $R^3$ or $R^4$ is ($C_1$–$C_6$)alkoxy or ($C_1$–$C_6$)alkoxy($C_1$–$C_6$)alkoxy.

Specific preferred compounds of formula I include the racemate and both R and S isomers of the following:

3-[4-(4-Fluorophenoxy)benzenesulfonylamino] tetrahydropyran-3-carboxylic acid hydroxyamide and 3-[4-(4-Chlorophenoxy)benzenesulfonylamino] tetrahydropyran-3-carboxylic acid hydroxyamide.

Other compounds of formula I include the racemate and both R and S isomers of the following:

3-[4-(Phenoxy)benzenesulfonylamino]tetrahydropyran-3-carboxylic acid hydroxyamide;

3-[4-(4-Pyridyloxy)benzenesulfonylamino] tetrahydropyran-3-carboxylic acid hydroxyamide;

3-[4-(4-Fluorophenyl)benzenesulfonylamino] tetrahydropyran-3-carboxylic acid hydroxyamide;

3-[4-(4-Fluorophenylmethoxy)benzenesulfonylamino] tetrahydropyran-3-carboxylic acid hydroxyamide;

3-[4-(Phenylmethoxy)benzenesulfonylamino] tetrahydropyran-3-carboxylic acid hydroxyamide;

3-[4-(4-Fluorophenylethoxy)benzenesulfonylamino] tetrahydropyran-3-carboxylic acid hydroxyamide;

3-[4-(4-Fluoro-phenoxy)-benzenesulfonylamino]-5-methyl-tetrahydro-pyran-3-carboxylic acid hydroxyamide;

3-[4-(4-Fluoro-phenoxy)-benzenesulfonylamino]-5-phenyl-tetrahydro-pyran-3-carboxylic acid hydroxyamide;

3-[4-(4-Chloro-phenoxy)-benzenesulfonylamino]-6-methoxy-tetrahydro-pyran-3-carboxylic acid hydroxyamide;

3-[4-(4-Chloro-phenoxy)-benzenesulfonylamino]-6-ethoxy-tetrahydro-pyran-3-carboxylic acid hydroxyamide;

3-[4-(4-Chloro-phenoxy)-benzenesulfonyl]-6-(2-methoxyethoxy)-tetrahydropyran-3-carboxylic acid hydroxyamide;

3-[4-(4-Chloro-phenoxy)-benzenesulfonylamino]-6-phenylmethoxy-tetrahydro-pyran-3-carboxylic acid hydroxyamide;

3-[4-(2,4-Difluoro-benzyloxy)-benzenesulfonylamino]-6-ethylthio-tetrahydro-pyran-3-carboxylic acid hydroxyamide;

3-[4-(2,4-Difluoro-benzyloxy)-benzenesulfonylamino]-6-propyl-tetrahydro-pyran-3-carboxylic acid hydroxyamide;

3-[4-(2,4-Difluoro-benzyloxy)-benzenesulfonylamino]-6-(3-phenylpropyl)-tetrahydro-pyran-3-carboxylic acid hydroxyamide;

3-[4-(2,4-Difluoro-benzyloxy)-benzenesulfonylamino]-6-(2-hydroxyethyl)-tetrahydro-pyran-3-carboxylic acid hydroxyamide;

3-[4-(2-Chloro-4-fluoro-benzyloxy)-benzenesulfonylamino]-6-(2-methoxyethyl)-tetrahydro-pyran-3-carboxylic acid hydroxyamide;

3-[4-(2-Chloro-4-fluoro-benzyloxy)-benzenesulfonylamino]-6-(2-phenylmethoxyethyl)-tetrahydro-pyran-3-carboxylic acid hydroxyamide;

3-[4-(2-Chloro-4-fluoro-benzyloxy)-benzenesulfonylamino]-6-phenyl-tetrahydro-pyran-3-carboxylic acid hydroxyamide;

3-[4-(2-Chloro-4-fluoro-benzyloxy)-benzenesulfonylamino]-6-(4-fluorophenyl)-tetrahydro-pyran-3-carboxylic acid hydroxyamide;

3-[4-(2-Chloro-4-fluoro-benzyloxy)-benzenesulfonylamino]-6-(3-pyridyl)-tetrahydro-pyran-3-carboxylic acid hydroxyamide;

3-[4-(4-Chloro-2-fluoro-benzyloxy)-benzenesulfonylamino]-6-(3-hydroxypropyl)-tetrahydro-pyran-3-carboxylic acid hydroxyamide;

3-[4-(4-Chloro-2-fluoro-benzyloxy)-benzenesulfonylamino]-6-(3-ethoxypropyl)-tetrahydro-pyran-3-carboxylic acid hydroxyamide;

3-[4-(4-Chloro-2-fluoro-benzyloxy)-benzenesulfonylamino]-6-(3-(2-phenylethoxy)propyl)-tetrahydro-pyran-3-carboxylic acid hydroxyamide;

3-[4-(2-Chloro-4-fluoro-benzyloxy)-benzenesulfonylamino]-6-hydroxy-6-methyl-tetrahydro-pyran-3-carboxylic acid hydroxyamide;

3-[4-(2-Chloro-4-fluoro-benzyloxy)-benzenesulfonylamino]-6-hydroxy-6-phenyl-tetrahydro-pyran-3-carboxylic acid hydroxyamide;

3-[4-(2-Chloro-4-fluoro-benzyloxy)-benzenesulfonylamino]-6-(4-fluorophenyl)-6-methoxy-tetrahydro-pyran-3-carboxylic acid hydroxyamide;

3-[4-(2-Chloro-4-fluoro-benzyloxy)-benzenesulfonylamino]-6-hydroxy-6-(2-hydroxyethyl)-tetrahydro-pyran-3-carboxylic acid hydroxyamide;

3-[4-(2-Chloro-4-fluoro-benzyloxy)-benzenesulfonylamino]-5,5-dimethyl-tetrahydro-pyran-3-carboxylic acid hydroxyamide;

3-[4-(2-Chloro-4-fluoro-benzyloxy)-benzenesulfonyl-amino]-5-hydroxy-5-methyl-tetrahydro-pyran-3-carboxylic acid hydroxyamide;

3-[4-(4-Chloro-phenoxy)-benzenesulfonylamino]-5,6-dimethyl-3,4-dihydro-2H-pyran-3-carboxylic acid hydroxyamide;

3-[4-(4-Chloro-phenoxy)-benzenesulfonylamino]-5-methyl-3,4-dihydro-2H-pyran-3-carboxylic acid hydroxyamide; and 3-[4-(4-Chloro-phenoxy)-benzenesulfonylamino]-6-methyl-3,4-dihydro-2H-pyran-3-carboxylic acid hydroxyamide.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity (preferably MMP-13) and other diseases characterized by mammalian reprolysin activity (preferably TACE or Aggrecanase activity most preferably TACE activity) in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of formula I or a pharmaceutically acceptable salt thereof effective in treating such a condition.

The present invention also relates to the treatment of diseases characterized by matrix metalloproteinase activity (preferably MMP-13 activity) and other diseases characterized by mammalian reprolysin activity (preferably TACE or Aggrecanase activity, most preferably TACE activity) in a mammal, including a human, comprising administering to said mammal an amount of a compound of formula I or a pharmaceutically acceptable salt thereof effective in treating such a condition.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The present invention also relates to a method for the inhibition of (a) matrix metalloproteinases or other metalloproteinases involved in matrix degradation, or (b) a mammalian reprolysin (such as aggrecanase or ADAM's T-1, 10, 12, 15 and 17, preferably ADAM-17) in a mammal, including a human, comprising administering to said mammal an effective amount of a compound of formula I or a pharmaceutically acceptable salt thereof.

The present invention also relates to inhibitors with differential metalloprotease activity. Specifically, for example, the present invention relates to a preferred group of compounds of the Formula I which selectively inhibit matrix metalloprotease-13 (MMP-13) preferentially over MMP-1. The present invention also relates to methods of treatment and pharmaceutical compositions of such selective MMP-13 inhibitors.

Another group of preferred inhibitors of formula I the inventors have been able to identify include those which selectively inhibit TACE preferentially over MMP-1. Another group of preferred inhibitors of formula I the inventors have been able to identify include those molecules which selectively inhibit Aggrecanase preferentially over MMP-1. Another group of preferred inhibitors of formula I the inventors have been able to identify include those molecules which selectively inhibit TACE and matrix metalloprotease-13 (MMP-13) preferentially over MMP-1. Another group of preferred inhibitors of formula I the inventors have been able to identify include those molecules which selectively inhibit Aggrecanase and matrix metalloprotease-13 (MMP-13) preferentially over MMP-1. Another group of preferred inhibitors of formula I the inventors have been able to identify include those molecules which selectively inhibit Aggrecanase and TACE preferentially over MMP-1. Another group of preferred inhibitors of formula I the inventors have been able to identify include those molecules which selectively inhibit Aggrecanase and matrix metalloprotease-13 (MMP-13) preferentially over MMP-1 and TACE.

This invention also encompasses pharmaceutical compositions containing prodrugs of compounds of the formula 1.

This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, hydroxamic acid, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), COX-2 inhibitors, low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate and with statins in combination with COX-2 inhibitors.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as Aricept, tacrine, COX-2 inhibitors, propentofylline or metryfonate.

The compounds of the present invention may also be used in combination with osteoporosis agents such as droloxifene or fosomax and immunosuppressant agents such as FK-506 and rapamycin.

DETAILED DESCRIPTION OF THE INVENTION

The following reaction Scheme illustrates the preparation of the compounds of the present invention. Unless otherwise indicated, $R^1$, $R^2$, $R^3$, $R^4$ and Q in the reaction Schemes and the discussion that follows is defined as above.

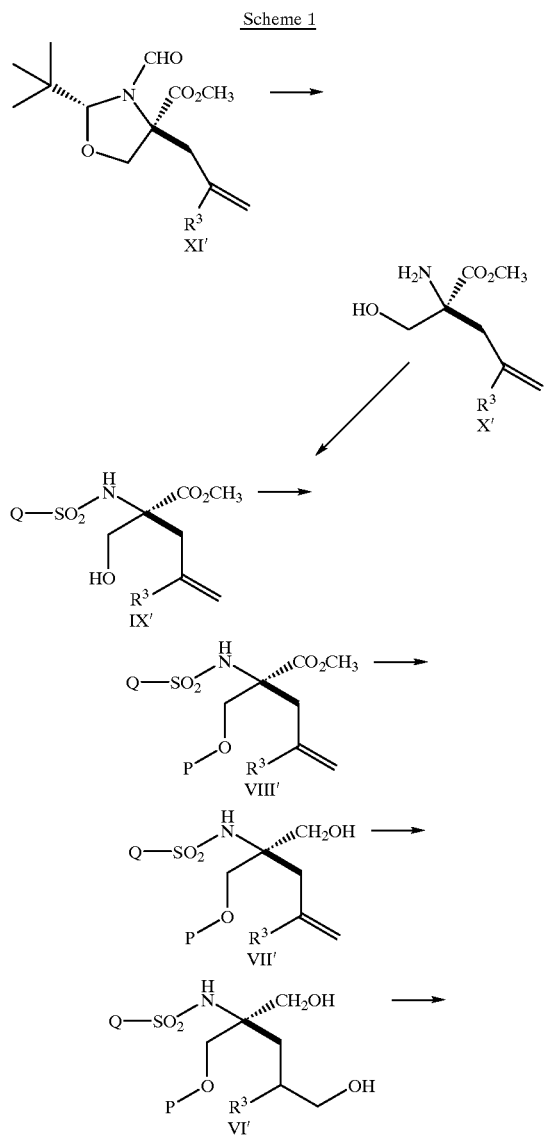

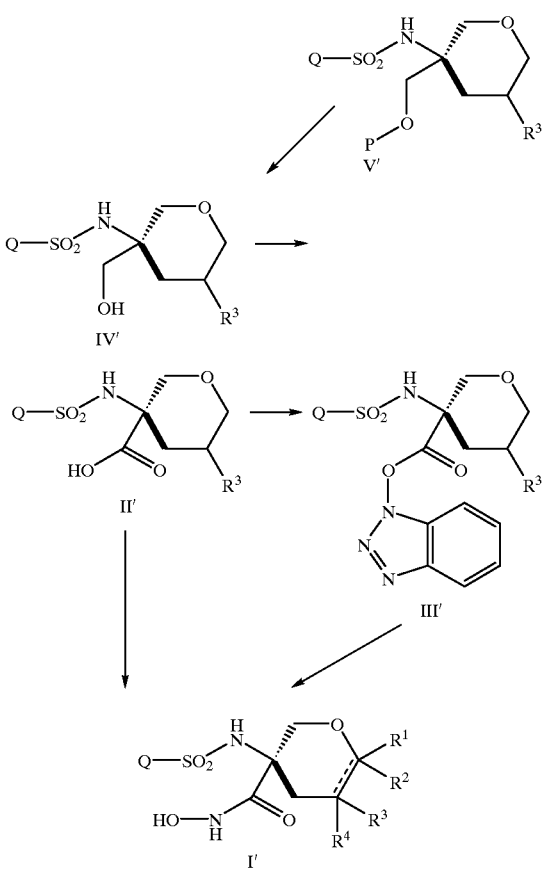

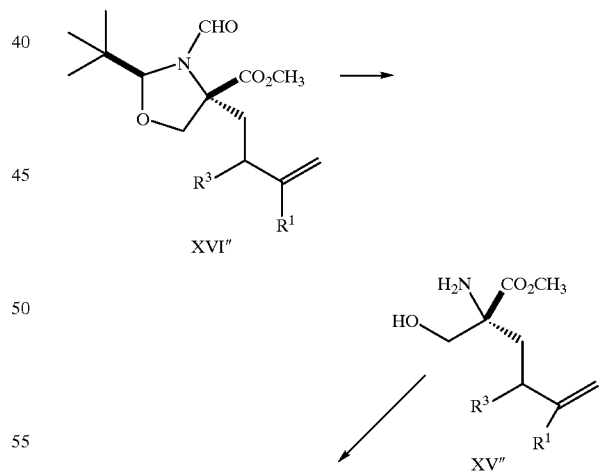

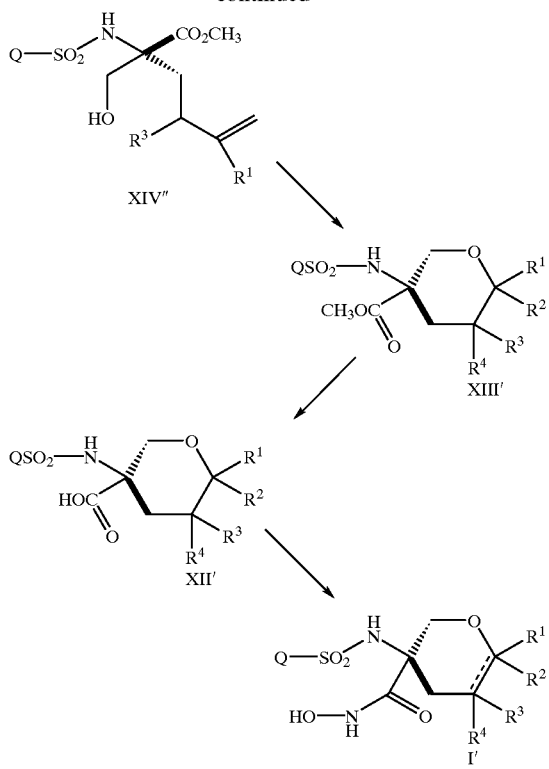

Scheme 1 refers to the preparation of compounds of the formula I', wherein one of $R^1$ or $R^2$ is hydrogen. Compounds of the formula I' are prepared from the L-serine-derived enantiomers of formula XI'. One skilled in the art will appreciate that Scheme I generically refers to the preparation of each of the enantiomers of formula I (i.e. I' and I") as well as the preparation of a racemic mixture of both enantiomers. The stereochemistry of the product is limited by the choice of starting material, i.e. L-serine-derived starting material of formula XI' produces product of formula I' and D-serine-derived starting material of formula XI" produces product of formula I".

Referring to Scheme 1, the compound of formula I' may be prepared from the carboxylic acid of formula II' by treatment with an activating agent such as 1-(3-dimethylaminopropyl-3-ethylcarbodiimide and 1-hydroxybenztriazole in a polar solvent, such as N,N-dimethylformamide, followed by the addition of hydroxylamine to the reaction mixture after a time period between about 15 minutes to about 1 hour, preferably about 30 minutes, at a temperature between about 0° C. to about 50° C., preferably about room temperature. The hydroxylamine is preferably generated in situ from a salt form, such as hydroxylamine hydrochloride, in the presence of a base, such as triethylamine.

Alternatively the compound of formula I' can be prepared from a compound of formula II' by reaction with a protected derivative of hydroxylamine or its salt form, where the hydroxyl group is protected as a tert-butyl, benzyl, allyl or 2-trimethylsilylethyl ether. Removal of the hydroxyl protecting group is carried out by hydrogenolysis for a benzyl protecting group (5% palladium on barium sulfate is the preferred catalyst) or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium(II)chloride. The 2-trimethylsilylethyl ether may be removed by reaction with a strong acid such as trifluoroacetic acid or by reaction with a fluoride source such as boron trifluoride etherate.

The reaction of II' with hydroxylamine, a salt of hydroxylamine, a protected derivative of hydroxylamine or a salt of a protected derivative of hydroxylamine may also be carried out in the presence of (benztriazol-1-yloxy)tris (dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

Another procedure for converting a compound of formula II' to a compound of formula I' is to react the compound of formula II' with O-benzylhydroxylamine hydrochloride in the presence of (benztriazol-1-yloxy)tris(dimethylamino) phosphonium hexafluorophosphate and triethylamine using methylene chloride as solvent. Subsequent removal of the O-benzyl protecting group to afford a compound of formula I' is then carried out by hydrogenolysis under 3 atmospheres of hydrogen at room temperature using 5% palladium on barium sulfate as catalyst. The preferred solvent is methanol. The reaction time may vary from about 1 hour to about 2 days (8 hours is preferred).

The preferred procedure for converting a compound of formula II' to a compound of formula I' is to react the compound of formula II' with oxalyl chloride in methylene chloride in the presence of a catalytic amount of DMF for 16 hours. The resulting acid chloride is reacted at 0° C. with N, O-bis trimethylsilyl hydroxylamine formed by reacting hydroxylamine hydrochloride with chlorotrimethyl-silane in pyridine at 0° C. to room temperature. The product of formula I' is obtained after about 2 to about 5 hours of reaction at about 0° C. to about 22° C. (i.e. room temperature) followed by an acidic aqueous workup which removes all trimethyl silyl residues.

In certain instances it is preferred to obtain the compound of formula I' by reaction of hydroxylamine, a salt of hydroxylamine, a protected derivative of hydroxylamine or a salt of a protected derivative of hydroxylamine with an activated ester of formula III'. The reaction is carried out in an inert solvent, such as N,N-dimethyl-formamide at a temperature ranging from about room temperature to about 80° C., preferably about 60° C. for a time period of about 1 hour to about 2 days. If a protected derivative of hydroxylamine or a salt of a protected derivative of hydroxylamine is used, removal of the protecting group is carried out as described above. The activated ester derivative of formula III' is obtained by treatment of the compound of formula II with (benztriazol-1-yloxy)tris(dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

The intermediate compound of formula II' is prepared by oxidation of a compound of formula IV'. The reaction is carried out in a solvent such as wet acetonitrile or acetone with a catalytic amount of chromium trioxide and a co-oxidant such as periodic acid or with an excess of Jones reagent, preferably with a catalytic amount of chromium trioxide and periodic acid as a co-oxidant. The reaction is carried out at a temperature of about 0° C. to about 80° C., preferably about 0° C. The reaction mixture is normally agitated for a time between about 10 minutes and about 1 day, preferably about 2 hours.

The compound of formula IV' is prepared by de-silylation of a compound of formula V', wherein P is a silyl protecting group of the formula $R^5R^6R^7Si-$, wherein $R^5$, $R^6$ and $R^7$ are each $(C_1-C_6)$alkyl. The reaction is carried out in a solvent such as THF, acetonitrile or methylene chloride with an excess of a fluoride source such as tetrabutyl ammonium fluoride, hydrogen fluoride in pyridine, boron trifluoride etherate, or cesium fluoride, preferably tetrabutyl ammonium fluoride in THF or in a solvent such as wet THF or wet methanol with an excess of a protic acid such as dilute hydrochloric acid, acetic acid or toluene sulfonic acid, preferably dilute hydrochloric acid. The reaction mixture is stirred at a temperature of from about 0° C. to about 80° C., preferably about 20° C. (room temperature) for a time period of about 10 minutes to about 2 days, preferably about 1 hour.

The compound of formula V' is prepared by treating a compound of formula VI' with a sulfonylating reagent such as triflic anhydride, mesyl anhydride, mesyl chloride or tosyl chloride, preferably triflic anhydride in the presence of a base such as 2,6-lutidine, pyridine, triethylamine, or diisopropylethylamine, preferably 2,6-lutidine in an inert solvent such as THF, acetonitrile, or methylene chloride, preferably methylene chloride at a temperature of from about 0° C. to about 80° C., preferably about 0° C. for a period of time from about 10 minutes to about 2 days, preferably about 2 hours.

The compound of formula VI' is prepared by hydroboration of a compound of formula VII' with a hydroborating reagent such as diborane or 9-bicycloboranonane (9-BBN), preferably 9-bicycloboranonane in an inert solvent such as THF or ether, preferably THF, at a temperature of from about 0° C. to about 80° C., preferably about 20° C. (room temperature), for a period of time from about 10 minutes to about 1 day, preferably about 3 hours. The reaction is oxidatively worked up using sodium perborate and water or dilute hydrogen peroxide and a base such as sodium hydroxide, preferably sodium perborate and water.

The compound of formula VII' is prepared by reduction of a compound of formula VIII' with a hydride reagent such as lithium aluminum hydride, lithium triethyl borohydride or lithium borohydride, preferably lithium triethyl borohydride, in an inert solvent solvent such as THF or ether, preferably THF, at a temperature of from about −70° C. to about 80° C., preferably about −60° C. to about room temperature for a period of time of from about 10 minutes to about 1 day, preferably about 1 hour.

The compound of formula VIII' is prepared by silylation of a compound of formula IX' with a silylating reagent of the formula $R^5R^6R^7Si-L$, such as t-butyldimethylsilyl triflate, t-butyldimethylsilyl chloride, triisopropyl triflate, or t-butyldiphenylsilyl triflate, preferably t-butyldimethylsilyl triflate, in the presence of a base such as 2,6-lutidine, pyridine, triethylamine, or diisopropylethylamine, preferably 2,6-lutidine, in a solvent such as THF, acetonitrile, or methylene chloride, preferably THF, at a temperature of from about −20° C. to about 80° C., preferably about −10° C. to about 20° C. (room temperature), for a period of time from about 10 minutes to about 1 day, preferably about 2 hours.

The compound of formula IX' is prepared by reacting a compound of formula X' with a reactive functional derivative of a sulfonic add ($QSO_2OH$), such as the sulfonyl chloride ($QSO_2Cl$), in the presence of a base. Suitable bases include sodium hydroxide, triethylamine or diisopropylethylamine, preferably triethylamine. Suitable solvents include dimethylformamide (DMF), methylene chloride, tetrahydrofuran, dioxane, water or acetonitrile, preferably DMF. The reaction mixture is stirred at a temperature between about 0° C. to about 50° C., preferably at about 20° C. to about 25° C. (i.e. room temperature), for a time period between about 10 minutes to about 2 days, preferably about 1 day.

The compounds of formula X and XI are prepared by the method described by Seebach et al. *Helvetica Chemica Acta*, 70, 1194–1216 (1987).

Scheme 2 refers to an alternate preparation of compounds of the formula I'. Compounds of the formula I' are prepared from the D-serine-derived enantiomers of formula XVII". One skilled in the art will appreciate that Scheme 2 generically refers to the preparation of each of the enantiomers of formula I (i.e. I' and I") as well as the preparation of a racemic mixture of both enantiomers. The stereochemistry of the product is limited by the choice of starting material, i.e. D-serine-derived starting material of formula XVII" produces product of formula I' and L-serine-derived starting material of formula XVII' produces product of formula I".

Referring to Scheme 2, the compound of formula I' can be prepared from compounds of the formula XII' by methods analogous to those for the conversion of compounds of the formula II' to formula I' in Scheme 1.

Compounds of the formula XII' can be prepared from compounds of the formula XIII' by saponification in the presence of a solvent, such as aqueous ethanol, with an excess of a metal hydroxide, such as sodium hydroxide or lithium hydroxide, at a temperature of about 20° C. to about 100° C., (i.e. room temperature to the reflux temperature of the solvent), preferably about 80° C. The reaction mixture is normally agitated at room temperature for a time period between about 30 minutes to about 1 week, preferably about 16 hours.

The compound of the formula XIII', wherein at least one of $R^1$ or $R^2$ is hydroxy, is prepared by ozonolysis of a compound of the formula XIV" in a solvent such as methanol or in a methanol/methylene chloride mixture, preferably in methanol, at a temperature of from −70° C. to 0° C., preferably about −70° C., for a period of time from about 5 minutes to about 1 hour, preferably about 10 minutes. The reaction is worked up by quenching with a reductant, such as dimethylsulfide or triphenylphosphine, preferably dimethylsulfide.

The compound of the formula XIII', wherein at least one of $R^1$ or $R^2$ is hydrogen, is prepared by reduction of a compound of formula XIII', wherein at least one of $R^1$ or $R^2$ is hydroxy, by treatment with a hydride donor such as triethylsilane in the presence of a Lewis or protic acid such as boron trifluoride etherate, trifluoroacetic acid or Amberlyst 15® ion exchange resin, preferably Amberlyst 15® ion exchange resin, in an inert solvent such as methylene chloride at a temperature of from 0° C. to 40° C., preferably about 20° C. (room temperature), for a period of time from about 10 minutes to about 1 day, preferably about 2 hours.

The compound of formula XIII', wherein at least one of $R^1$ or $R^2$ is other than hydroxy, $(C_1-C_6)$alkoxy, $(C_1-C_6)$alkoxy$(C_1-C_6)$alkoxy, $((C_1-C_6)$alkyl$)_2$amino$(C_1-C_6)$alkoxy, $(C_1-C_6)$alkylthio, $(C_6-C_{10})$aryl$(C_1-C_6)$alkoxy, $(C_2-C_9)$heteroaryl$(C_1-C_6)$alkoxy, $(C_6-C_{10})$aryl$(C_1-C_6)$alkythio or $(C_2-C_9)$heteroaryl$(C_1-C_6)$alkythio, is prepared by reaction of the cyclic hemiacetal-containing intermediate of formula XIII' (i.e. wherein one of $R^1$ or $R^2$ is hydroxy or the methyl or ethyl derivative thereof) with allyl trimethyl silane and trimethylsilyl triflate. The allyl group can then be modified by methods known in the art to yield compounds containing an $R^1$ or $R^2$ group as defined above. For example, the allyl group can be hydrogenated over a Pd catalyst yielding a compound wherein $R^1$ or $R^2$ is $(C_1-C_6)$alkyl. Alternatively, the allyl group could be hydroborated with diborane or 9-bicycloboranonane and oxidatively worked up yielding a compound wherein $R^1$ or $R^2$ is hydroxy$(C_1-C_6)$ alkyl. The allyl group could be reacted with an $(C_6-C_{10})$aryl iodide or bromide such a iodobenzene under conditions known as the "Heck reaction" and then hydrogenated yielding a compound wherein $R^1$ or $R^2$ is $(C_6-C_{10})$aryl$(C_1-C_6)$ alkyl. The hydroxy$(C_1-C_6)$alkyl compound produced by the method described above could be alkylated with an alkyl or arylalkyl iodide, bromide or triflate yielding a compound wherein $R^1$ or $R^2$ $(C_1-C_6)$alkoxy$(C_1-C_6)$alkyl or $(C_6-C_{10})$ aryl$(C_1-C_6)$alkoxy$(C_1-C_6)$alkyl. Methods for carrying out these reactions are well know to those skilled in the art and can be found in a reference source such as "Advanced Organic Chemistry" by Jerry March (4th Edition, John Wiley & Sons, Inc. 1992).

The compound of formula XIII', wherein at least one of $R^1$ or $R^2$ is $(C_1-C_6)$alkoxy, $(C_1-C_6)$alkoxy$(C_1-C_6)$alkoxy, $((C_1-C_6)$alkyl$)_2$amino$(C_1-C_6)$alkoxy, $(C_1-C_6)$alkylthio, $(C_6-C_{10})$aryl$(C_1-C_6)$alkoxy, $(C_2-C_9)$heteroaryl$(C_1-C_6)$ alkoxy, $(C_6-C_{10})$aryl$(C_1-C_6)$alkythio or $(C_2-C_9)$heteroaryl $(C_1-C_6)$alkythio, is prepared by reaction of the cyclic hemiacetal-containing compound of formula XIII' (or the methyl or ethyl derivative thereof) with a compound of the formula $R^1H$ or $R^2H$, wherein $R^1$ or $R^2$ is $(C_1-C_6)$alkoxy, $(C_1-C_6)$alkoxy$(C_1-C_6)$alkoxy, $((C_1-C_6)$alkyl$)_2$amino $(C_1-C_6)$alkoxy, $(C_1-C_6)$alkylthio, $(C_6-C_{10})$aryl$(C_1-C_6)$ alkoxy, $(C_2-C_9)$heteroaryl$(C_1-C_6)$alkoxy, $(C_6-C_{10})$aryl $(C_1-C_6)$alkythio or $(C_2-C_9)$heteroaryl$(C_1-C_6)$alkythio, in the presence of an acid such as toluene sulfonic acid or camphor sulfonic acid in a solvent such as tetrahydrofuran, benzene or toluene for a period from about 1 hour to about 3 days at a temperature from about 0° C. to about 50° C., preferably about 20° C. and about 1 day.

The compounds of formula XIV", XV" and XVI" can be prepared by methods analogous to the methods for the conversion of compounds of formula IX' to XI' according to Scheme 1.

The isomeric compounds, I", are prepared in the same manner as described above in Schemes 1 and 2 but starting with the isomer of compound XI' or XVII" derived from D-serine (Scheme 1) or L-serine (Scheme 2) rather than from L-serine (Scheme 1) or D-serine (Scheme 2). Alternatively, stereochemistry of intermediate VII (i.e. VII' or VII", respectively) can be inverted so as to prepare compounds of formula I with the opposite stereochemistry (i.e. I" or I' respectively) by transforming compound VII' into VII" through the intermediacy of compound XVIII (i.e. XVIII' or XVIII", respectively) as shown in Scheme 3.

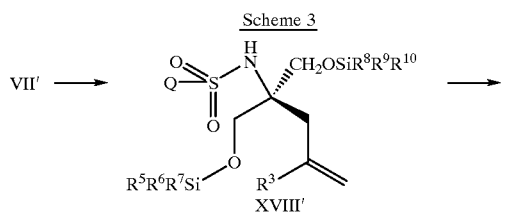

Scheme 3

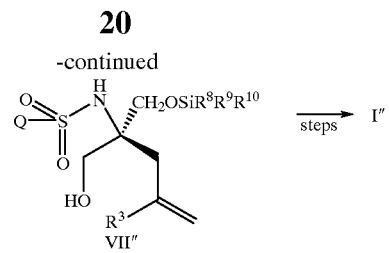

Compounds of formula XVIII' are prepared by silylation of a compound of formula VII' using the same method as for the preparation of VIII', in Scheme 1. Through the proper choice of the —$SiR^5R^6R^7$ and —$SiR^8R^9R^{10}$ groups a compound of formula XVIII' can be converted to a compound of formula VII" by treatment with protic acids such as dilute hydrochloric acid, acetic acid, or toluene sulfonic acid, preferably dilute hydrochloric acid, in a solvent such as methanol or THF, preferably methanol, at a temperature of from about 0° C. to about 80° C., preferably about 20° C. (room temperature), for a period of time of from about 10 minutes to about 2 days, preferably about 2 hours. Proper choices of the —$SiR^5R^6R^7$ and —$SiR^8R^9R^{10}$ would include —$Si(CH_3)_3$ for —$SiR^5R^6R^7$ and —$Si(isopropyl)_3$, —$Si(t$-butyl$)(CH_3)_2$, or —$Si(t$-butyl$)(phenyl)_2$ for —$SiR^8R^9R^{10}$ or —$Si(t$-butyl$)(CH_3)_2$ for —$SiR^5R^6R^7$ and —$Si(isopropyl)_3$ or —$Si(t$-butyl$)(phenyl)_2$ for —$SiR^8R^9R^{10}$.

The compound of formula VII" is converted to the compound of formula I" by the same procedures as used for converting VII' to I' in Scheme 1.

The racemic compound I is prepared from racemic 2-amino-2-hydroxymethyl-4-pentenoic acid methyl acid, which can be prepared by methods know in the art, using the same procedures used to convert X' into I' in Scheme 1.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

BIOLOGICAL ASSAYS

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the mammalian reprolysin activity (such as the production of tumor necrosis factor) is shown by the following in vitro assay tests.

MMP Assays

Collagenase-3 (matrix metalloproteinase-13) selective inhibitors as used herein refers to agents which exhibit at least a 100 fold selectivity for the inhibition of collagenase-3 enzyme activity over collagenase-1 enzyme activity and a potency of less than 100 nM as defined by the $IC_{50}$ results from the MMP-13/MMP-1 fluorescence assays described below. Collagenase-3 selective inhibitors can be identified by screening the inhibitors of the present invention through the MMP-13/MMP-1 fluorescence assays described below and selecting those agents with MMP-13/MMP-1 inhibition $IC_{50}$ ratios of 100 or greater and potency of less than 100 nM.

Non-selective collagenase inhibitors as used herein refer to agents which exhibit less than a 100 fold selectivity for the inhibition of collagenase-3 enzyme activity over collagenase-1 enzyme activity or a potency of more than 100 nM as defined by the $IC_{50}$ results from the MMP-13/MMP-1 fluorescence assays described below.

The ability of collagenase inhibitors to inhibit collagenase activity is well known in the art. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→>1.2 μM→>0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1-D6.

Collagenase-1 is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys (NMA)-$NH_2$) is made as a 5 mM stock in dimethylsulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 μM then the inhibitors are assayed at concentrations of 0.3 μM, 0.03 μM, and 0.003 μM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

10 mM→120 $\mu$M→12 $\mu$M→1.2 $\mu$M→0.12 $\mu$M

Further dilutions are made as necessary following this same scheme. A minimum of four inhibitor concentrations for each compound are performed in each assay. 25 $\mu$L of each concentration is then added to triplicate wells of a black 96 well U-bottomed microfluor plate. As the final assay volume is 100 $\mu$L, final concentrations of inhibitor are the result of a further 1:4 dilution (i.e. 30 $\mu$M→3 $\mu$M→0.3 $\mu$M→0.03 $\mu$M, etc.). A blank (no enzyme, no inhibitor) and a positive enzyme control (with enzyme, no inhibitor) are also prepared in triplicate.

Activated enzyme is diluted to 200 ng/mL in assay buffer, 25 $\mu$L per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 $\mu$M. The assay is initiated by addition of 50 $\mu$L of diluted substrate yielding a final assay concentration of 3 $\mu$M substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 $\mu$M) under similar conditions as described above for the inhibition of human collagenase (MMP-1).

Human recombinant 92 kD gelatinase (MMP-9, gelatinase B) is activated for 2 hours with 1 mM p-aminophenyl-mercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM $CaCl_2$, 20 $\mu$M $ZnCl_2$, 0.02% BRIJ-35 (vol./vol.)) using the following scheme:

10 mM→120 $\mu$M→12 $\mu$M→1.2 $\mu$M→0.12 $\mu$M

Further dilutions are made as necessary following this same scheme. A minimum of four inhibitor concentrations for each compound are performed in each assay. 25 $\mu$L of each concentration is then added to triplicate wells of a black 96 well U-bottomed microfluor plate. As the final assay volume is 100 $\mu$L, final concentrations of inhibitor are the result of a further 1:4 dilution (i.e. 30 $\mu$M→3 $\mu$M→0.3 $\mu$M→0.03 $\mu$M, etc.). A blank (no enzyme, no inhibitor) and a positive enzyme control (with enzyme, no inhibitor) are also prepared in triplicate.

Activated enzyme is diluted to 100 ng/mL in assay buffer, 25 $\mu$L per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 $\mu$M. The assay is initiated by addition of 50 $\mu$L of diluted substrate yielding a final assay concentration of 10 $\mu$M substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 $\mu$M zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 $\mu$M, 3 $\mu$M, 0.3 $\mu$M, and 0.03 $\mu$M.

Substrate (Dnp-Pro-Cha-Gly-Cys(Me)-His-Ada-Lys(NMA)-$NH_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Collagen film MMP-13 Assay

Rat type I collagen is radiolabeled with $^{14}C$ acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 uM $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 µl of appropriate drug dilution and 100 µl of diluted enzyme are pipetted into wells of a 96 well plate containing collagen films labeled with $^{14}C$-collagen. The final enzyme concentration is 0.3 µg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1a (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 µg/ml trypsin is added to each well and incubation continued for a further 48 hours at 37° C. After 48 hours incubation in trypsin, the PBS solution is removed. Aliquots (50 µl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human Monocyte Assay

Human mononuclear cells were isolated from anticoagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFa using the R&D ELISA Kit.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 µCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1%PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. |
| | Make a 100 uM stock of each compound in DMEM in 96 well plate. Store in freezer overnight. |
| | The next day perform serial dilutions in DMEM with IL-1 to 5 uM, 500 nM, and 50 nM. |
| | Aspirate final wash from wells and add 50 ul of compound from above dilutions to 450 ul of IL-1 media in appropriate wells of the 48 well plates. |
| | Final compound concentrations equal 500 nM, 50 nM, and 5 nM. |
| | All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50 % release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

The compounds of the present invention that were tested all have $IC_{50}$'s in at least one of the above assays of less than 100 µM preferably less than 100 nM. Certain preferred groups of compounds possess differential selectivity toward the various MMP's or ADAMs. One group of preferred compounds possess selective activity towards MMP-13 over MMP-1. Another preferred groups of compounds possess aggrecanase activity in addition to selectivity for MMP-13 over MMP-1.

For administration to mammals, including humans, for the inhibition of matrix metalloproteinases (preferably inhibition of MMP-13, most preferably MMP-13 selective over MMP-1) or mammalian reprolysin, a variety of conventional routes may be used including oral, parenteral (e.g., intravenous, intramuscular or subcutaneous), buccal, anal and topical. In general (preferably oral), the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject. The compounds of the present invention may also be administer in sustained delivery formulations.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. In the case of animals, compounds can be administered intranasally at dosage levels of about 0.2 to 10 mg/kg/day given in a single dose or up to 3 divided doses.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The following Examples illustrate the preparation of the compounds of the present invention. Melting points are uncorrected. NMR data are reported in parts per million (δ) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

(R) 3-[4-(4-Fluoro-phenoxy-benzenesulfonylamino]-tetrahydro-pyran-3-carboxylic acid hydroxyamide

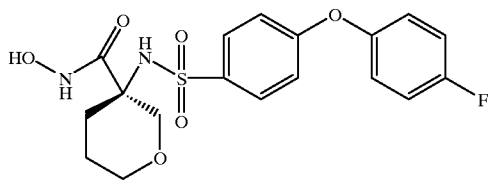

(S) 2-[4-(4-Fluoro-phenoxy)-benzenesulfonylamino]-2-hydroxymethyl-pent-4-enoic acid methyl ester (S) 2-Amino-2-hydroxymethyl-pent-4-enoic acid methyl ester (4.15 g, 26.0 mmole) was treated with 4-(4-fluoro-phenoxy)-benzenesulfonyl chloride (8.03 g, 28.0 mmole) and diisopropylethyl amine (4.01 g, 31.0 mmole) in dimethylformamide (25 mL) at room temperature for 18 hours. The reaction mixture was then partitioned between ethyl acetate (100 mL) and 0.5N hydrochloric acid (100 mL). The separated aqueous layer was extracted with ethyl acetate (2×100 mL). The combined organic layers were washed with water (2×), dried over anhydrous magnesium sulfate (MgSO$_4$), filtered and concentrated in vacuo to give 7.75 g of an oil. This was chromatographed yielding 4.37 g (41%) of the title compound as an orange oil.

$^1$H NMR (CDCl$_3$) δ: 2.41 (1H, dd), 2.54 (1H, dd), 2.60 (1H, dd), 3.66 (3H, s), 3.87 (1H, dd), 4.02 (1H, dd), 5.05 (1H, dd), 5.08 (1H, dd), 5.45 (1H, m), 5.55 (1H, s), 6.9–7.2 (6H, m), 7.84 (2H, d). Mass spectrum (APCl) M$^+$+1: 410 mu.

(S) 2-(tert-Butyl-dimethyl-silanyloxymethyl)-2-[4-(4-fluoro-phenoxy)-benzenesulfonyl amino]-pent-4-enoic acid methyl ester (S) 2-[4-(4-Fluoro-phenoxy)-benzenesulfonylamino]-2-hydroxymethyl-pent-4-enoic acid methyl ester (630 mg, 1.53 mmole) and 2,6-lutidine (0.445 mL, 3.8 mmole) in methylene chloride was treated with t-butyldimethylsilyl triflate (TBDMSOTf) (0.460 mL, 2.0 mmole) at −16° C. After 30 minutes at −10° C. and 1 hour at room temperature, the mixture was cooled back to −10° C. and additional 2,6-lutidine (0.250 mL) and TBDMSOTf (0.250 mL) was added. After slowly coming to room temperature the reaction mixture was diluted with ethyl acetate (25 mL) and water (25 mL). The organic layer was washed with 0.3M potassium sulfate (KHSO$_4$), water, and saturated sodium chloride solution. The extract was dried over MgSO$_4$, filtered and concentrated in vacuo to give 1.03 g of yellow oil. This was chromatographed to give 523 mg (65%) of the title compound as a colorless oil.

$^1$H NMR (CDCl$_3$) δ: −0.09 (3H, s), −0.07 (3H, s), 0.77 (9H, s), 2.44 (1H, dd), 2.78 (1H, dd), 3.65 (3H, s), 3.72 (1H, d), 3.87 (1H, d), 5.00 (2H, d), 5.43 (1H, s), 5.52 (1H, m), 6.92 (2H, d), 7.00 (2H, dd), 7.06 (2H, dd), 7.81 (2H, dd). Mass spectrum (APCl) M$^+$+1: 522 mu.

(R) N-[1-(tert-Butyl-dimethyl-silanyloxymethyl)-1-hydroxymethyl-but-3-enyl]-4-(4-fluoro-phenoxy)-benzenesulfonamide (S) 2-(tert-Butyl-dimethyl-silanyloxymethyl)-2-[4-(4-fluoro-phenoxy)-benzenesulfonylamino]-pent-4-enoic acid methyl ester (500 mg, 0.95 mmole) in THF was cooled to −60° C. and treated with lithium aluminum hydride solution (1.43 mL, 1.43 mmole at 1.0M in THF) while keeping the reaction temperature below −50° C. The mixture was allowed to warm slowly to room temperature. The reaction mixture was then quenched with water (55 µL), 15% NaOH solution (55 L), and water (165 µL). The reaction mixture was filtered through Celite® and the filter pad washed with ethyl acetate. The filtrate was concentrated in vacuo and the residue partitioned between ethyl acetate and water. The separated organic layer was dried over MgSO$_4$, filtered and concentrated in vacuo to give 327 mg of a yellow oil. This was chromatographed yielding 262 mg (56%) of the title compound as a colorless oil.

$^1$H NMR (CDCl$_3$) δ: 0.03 (6H, s), 0.87 (9H, s), 2.21 (1H, dd), 2.31 (1H, dd), 3.46 (1H, d), 3.59 (1H, d), 3.63 (2H, s), 5.0–5.1 (3H, m), 5.60 (1H, m), 6.98 (2H, d), 7.0–7.1 (4H, m), 7.82 (2H, d). Mass spectrum (APCI) M$^+$−1: 494 mu.

(R) N-[1-(tert-Butyl-dimethyl-silanyloxymethyl)-4-hydroxy-1-hydroxymethyl-butyl]-4-(4-fluoro-phenoxy)-benzenesulfonamide (R) N-[1-(tert-Butyl-dimethyl-silanyloxymethyl)-1-hydroxymethyl-but-3-enyl]-4-(4-fluoro-phenoxy)-benzenesulfonamide (250 mg, 0.504 mmole) in THF (1.5 mL) was treated with a solution of 9-bicycloboranonane (9-BBN) (3.54 mL, 3.5 mmole, 0.5M in THF) at room temperature for 3 hour. The reaction was quenched with water and sodium perborate tetrahydrate (808 mg, 5.25 mmole) added. After stirring vigorously for 1 hour, the solids were filtered off and washed with ethyl acetate. The filtrate was concentrate in vacuo and the residue partitioned between ethyl acetate (50 mL) and water (50 mL). The separated organic layer was washed with saturated sodium chloride solution (50 mL), dried over MgSO$_4$, filtered and concentrated in vacuo to give 476 mg of a turbid oil. This was chromatographed yielding 178 mg (69%) of a colorless oil which crystallized upon standing.

$^1$H NMR (CDCl$_3$) δ: 0.02 (6H, s), 0.86 (9H, s), 1.4–1.7 (4H, m), 3.4–3.5 (3H, m), 3.5–3.6 (3H, m), 5.26 (1H, br s), 6.97 (2H, d), 7.0–7.1 (4H, m), 7.83 (2H, d). Mass spectrum (APCI) M$^+$−1: 512 mu.

(R) N-[3-(tert-Butyl-dimethyl-silanyloxymethyl)-tetrahydro-pyran-3-yl]4-(4-fluoro-phenoxy)-benzenesulfonamide (R) N-[1-(tert-Butyl-dimethyl-silanyloxymethyl)-4-hydroxy-1-hydroxymethyl-butyl]-4-(4-fluoro-phenoxy)-benzenesulfonamide (530 mg, 1.03 mmole) and 2,6-lutidine (266 mg, 2.5 mmole) in methylene chloride (10 mL) were treated with triflic anhydride (0.21 mL, 1.24 mmole) at 0° C. After 2 hours at 0° C. the reaction warmed slowly to room temperature. The reaction mixture was diluted with methylene chloride (40 mL) and washed with saturated sodium bicarbonate solution (50 mL), 0.5N hydrochloric acid (50 mL) and water. The organic layer was dried over disodium sulfate (Na$_2$SO$_4$), filtered and concentrated in vacuo to give 562 mg of a viscous oil. This was chromatographed yielding 345 mg (67%) of the title compound as an oil.

$^1$H NMR (CDCl$_3$) δ: 0.02 (6H, s), 0.87 (9H, s), 1.4–1.7 (3H, m), 2.05 (1H, m), 3.4–3.6 (5H, m), 3.71 (1H, d), 5.00 (1H, s), 6.97 (2H, d), 7.0–7.1 (4H, m), 7.82 (2H, d). Mass spectrum (APCI) M$^+$−1: 494

(S) 4-(4-Fluoro-phenoxy)-N-(3-hydroxymethyl-tetrahydro-pyran-3-yl)-benzenesulfonamide (R) N-[3-(tert-Butyl-dimethyl-silanyloxymethyl)-tetrahydro-pyran-3-yl]-4-(4-fluoro-phenoxy)-benzenesulfonamide (330 mg, 0.666 mmole) was treated with tetrabutylammonium fluoride solution in THF (5.0 mL, 5.0 mmole, 1.0 M in THF) for 1 hour. The reaction mixture was then concentrated in vacuo and the residue taken up in methylene chloride (25 mL). This solution was washed with water (10 mL) and saturated sodium chloride solution (10 mL). The organic layer was dried over Na$_2$SO$_4$, filtered and concentrated in vacuo to give 211 mg (83%) of the title compound as a colorless oil.

$^1$H NMR (CDCl$_3$) δ: 1.40 (2H, m), 1.56 (1H, m), 1.72 (1H, m), 3.30 (1H, d), 3.41 (1H, m), 3.53 (1H, d), 3.73 (2H, m), 3.79 (1H, d), 5.09 (1H, s), 6.99 (2H, d), 7.0–7.1 (4H, m), 7.86 (2H, d). Mass spectrum (APCI) M$^+$−1: 380 mu.

(R) 3-[4-(4-Fluoro-phenoxy)-benzenesulfonylamino]-tetrahydro-pyran-3-carboxylic acid (S) 4-(4-Fluoro-phenoxy)-N-(3-hydroxymethyl-tetrahydro-pyran-3-yl)-benzenesulfonamide (200 mg, 0.524 mmole) in wet (20 µL water) acetonitrile (2.6 mL) was treated with a solution of periodic acid and chromium trioxide (3.0 mL of 11.4 g of periodic acid H$_5$IO$_6$ and 23 mg of chromate CrO$_3$ in 114 mL of wet (0.75 vol %) acetonitrile) at 0° C. After 2 hours at 0° C. the reaction was quenched with Na$_2$HPO$_4$ solution (600 mg in 10 mL water). The reaction was then concentrated in vacuo and ethyl acetate (25 mL) added. This solution was washed with disodium phosphate (Na$_2$HPO$_4$) solution and 50% saturated sodium chloride solution. The combined aqueous layers were extracted with ethyl acetate (2×) and the combined organic layers were dried over MgSO$_4$, filtered and concentrated in vacuo to give 195 mg of a white foam. Chromatography of this yielded 152 mg (73%) of the title compound as a white foam.

$^1$H NMR (CDCl$_3$) δ: 1.55 (1H, m), 1.68 (1H, m), 2.13 (1H, m), 2.22 (1H, m), 3.49 (1H, m), 3.7–3.8 (2H, m), 3.83 (1H, d), 5.38 (1H, s), 6.97 (2H, d), 7.0–7.1 (4H, m), 7.85 (2H, d). Mass spectrum (APCI) M$^+$−1: 394 mu. Rotation [a]$_D$ (MeOH, c=1.0)+3.5°.

(R) 3-[4-(4-Fluoro-phenoxy)-benzenesulfonylamino]-tetrahydro-pyran-3-carboxylic acid hydroxyamide Hydroxylamine hydrochloride (32 mg, 0.460 mmole) was treated with trimethylsilylchloride (134 µL, 1.06 mmole) in dry pyridine (200 µL) at 0° C. and allowed to stir at room temperature for 18 hours. (R) 3-[4-(4-Fluoro-phenoxy)-benzenesulfonylamino]-tetrahydro-pyran-3-carboxylic acid (140 mg, 0.354 mmole) was treated with oxalyl chloride (34 µL, 0.389 mmole) and dimethylformamide (1 µL) in methylene chloride (2.0 mL) at room temperature for 4 hours. Both solutions were cooled to 0° C. and the methylene chloride solution added to the pyridine solution and stirred at 0° C. for 1 hour and at room temperature for 18 hours. The reaction was quenched with 1N hydrochloric acid (14 mL). After 1 hour the mixture was extracted with ethyl acetate and washed with water. The separated ethyl acetate layer was dried over Na$_2$SO$_4$, filtered and concentrated in vacuo to give 118 mg (81%) of a white foam.

$^1$H NMR (CDCl$_3$) δ: 1.51 (1H, m), 1.58 (1H, m), 2.03 (1H, m), 2.10 (1H, m), 3.50 (1H, m), 3.69 (1H, d), 3.74 (1H, m), 4.04 (1H, d), 5.89 (1H, s), 6.97 (2H, d), 7.0–7.1 (4H, m), 7.82 (2H, d). Mass spectrum (APCI) M$^+$−1: 409 mu. Rotation [a]$_D$ (methanol, c=0.98)+17.2°.

HPLC retention time: 4.8 min (Waters NovaPack C$_{18}$ 3.9 mm×15 cm, 1.0 mL/min acetonitrile/water gradient, 30% acetonitrile to 90% acetonitrile, Δ2%/min).

Using the same procedures as in Example 1 and with the appropriate QSO$_2$Cl, the following example was also prepared:

EXAMPLE 2

(R) 3-[4-(4-Chloro-phenoxy-benzenesulfonylamino]-tetrahydro-pyran-3-carboxylic Acid Hydroxyamide Melting Point 154–155° C. $^1$H NMR (CDCl$_3$) δ: 1.51 (1H, m), 1.58 (1H, m), 2.03 (1H, m), 2.08 (1H, m), 3.50 (1H, m), 3.70 (2H, m), 4.11 (1H, d), 5.98 (1H, s), 6.99 (4H, m), 7.34 (2H, d), 7.84 (2H, d), 8.14 (1H, br s), 9.70 (1H, br s). Mass spectrum (APCl) M$^+$–1: 425/427 mu.

HPLC retention time: 9.6 min (Waters NovaPack C$_{18}$ 3.9 mm×15 cm, 1.0 mL/min acetonitrile/water gradient, 30% acetonitrile to 90% acetonitrile, Δ2%/min).

PREPARATION A 4-(4-Fluorophenoxy)benzenesulfonyl Chloride

Chlorosulfonic acid (26 mL, 0.392 mole) was added dropwise to ice-cooled 4-fluorophenoxybenzene (36.9 grams, 0.196 mole) with mechanical stirring. When addition was complete, the mixture was stirred at room temperature for 4 hours. The mixture was then poured into ice water. The product, 4-(4-fluorophenoxy)benzene-sulfonylchloride (18.6 grams, 33%) was collected by filtration and dried in the air.

PREPARATION B

Sodium 4-(3-Methylbutoxy)benzenesulfonate

A solution of 4-hydroxybenzenesulfonic acid (10.0 grams, 43.1 mmole) and sodium hydroxide (3.3 grams, 83 mmole) in water (40 mL) was mixed with a solution of 1-iodo-3-methylbutane (11.3 mL, 86.4 mmole) in isopropanol (60 mL) and the resulting mixture was heated at reflux for 2 days. The isopropanol was removed by evaporation under vacuum. The title compound, 10.0 grams (87%), was collected by filtration and washed with isopropanol.

PREPARATION C 4-(3-Methylbutoxy)benzenesulfonyl Chloride

A mixture of sodium 4-(3-methylbutoxy) benzenesulfonate (2.5 grams, 9.4 mmole), thionyl chloride (10 mL), and 5 drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the title compound as an oil, 2.34 grams (95%).

PREPARATION D

Sodium 4-(2-Cyclopentylethoxy)benzenesulfonate

A solution of 4-hydroxybenzenesulfonic acid (6.5 grams, 28.2 mmole) and sodium hydroxide (2.2 grams, 55 mmole) in water (15 mL) was mixed with a solution of 2-(bromoethyl)cyclopentane (15.0 grams, 84.7 mmole) in isopropanol (40 mL) and the resulting mixture was heated at reflux for 2 days. The isopropanol was removed by evaporation under vacuum. The titled compound, 4.7 grams (57%), was collected by filtration and washed with isopropanol.

PREPARATION E 4-(3-Methylbutoxy)benzenesulfonyl Chloride

A mixture of sodium 4-(2-cyclopentylethoxy)-benzenesulfonate (2.5 grams, 8.6 mmole), thionyl chloride (15 mL), and a few drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the title compound as an oil, 2.24 grams (90%).

PREPARATION F

4-Fluorobiphenylsulfonyl Chloride

Chlorosulfonic acid (8.7 mL, 0.13 mole) was added dropwise to 4-fluorobiphenyl (10.2 grams, 59 mmol) while stirring in an ice bath. Stirring was continued with ice cooling for 0.5 hours and then the reaction mixture was poured onto ice. The resulting white precipitate was collected by filtration and dissolved in chloroform. The chloroform solution was washed with water and brine, dried over magnesium sulfate and concentrated to afford a white solid. The desired product, 4-fluorobiphenylsulfonyl chloride (4.3 grams, 27%), was separated from 4-fluorobiphenylsulfonic acid (an unwanted side product) by crystallization of the latter from ethyl acetate and crystallization of the remaining material from hexane.

PREPARATION G

Sodium 4-(4-Fluorobenzyloxy)benzenesulfonate

To a solution of 4-hydroxybenzenesulfonic acid (5.13 grams, 22.1 mmole) in 1N aqueous sodium hydroxide solution (23 mL) was added a solution of 4-fluorobenzylbromide (3.3 mL, 26.5 mmole) in ethanol (20 mL). The resulting mixture was heated at reflux for 2 days. Upon cooling and standing, a white solid precipitated. The precipitated product, sodium 4-(4-fluorobenzyloxy) benzenesulfonate, 4.95 grams (74%) was collected by filtration and washed with ethyl acetate and diethyl ether.

PREPARATION H 4-(4-Fluorobenzyloxy)benzenesulfonyl Chloride

To a slurry of sodium 4-(4-fluorobenzyloxy) benzenesulfonate (0.5 grams, 1.64 mmole), in methylene chloride (5 mL) was added phosphorus pentachloride (275 mg, 1.31 mmole). The resulting mixture was heated at reflux for 7 hours. After cooling in an ice bath and quenching with water (15 mL), the mixture was extracted with ethyl acetate. The organic phase was washed with brine, dried over sodium sulfate, and concentrated to afford 4-(4-fluorobenzyloxy)benzenesulfonyl chloride a white solid (130 mg, 26%).

PREPARATION I 4-(4-Chlorophenoxy)benzenesulfonyl Chloride

Chlorosulfonic acid (9.7 mL, 0.147 mole) was added dropwise to 4-chlorophenoxybenzene (12.6 mL, 73.4 mmole) at room temperature with stirring. When addition was complete, the mixture was stirred at room temperature for 1 hour and then poured into ice water. The solid was collected by filtration, dried in the air, and recrystallized from petroleum ether and ethyl acetate to give 4-(4-chlorophenoxy)benzenesulfonylchloride (7.43 grams, 33%).

What is claimed is:

1. A compound of the formula

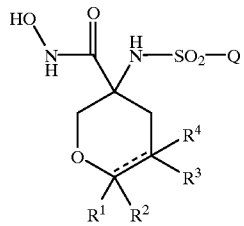

I wherein the dotted line represents an optional double bond, $R^1$, $R^2$, $R^3$, $R^1$ are each independently selected from the group consisting of hydrogen, hydroxy-, $(C_1-C_6)$alkyl-, $(C_1-C_6)$alkoxy-, $(C_1-C_6)$alkoxy$(C_1-C_6)$alkoxy-, $((C_1-C_6)$alkyl$)_2$amino$(C_1-C_6)$alkoxy-, $(C_1-C_6)$alkylthio-, $(C_6-C_{10})$aryl$(C_1-C_6)$alkoxy-, $(C_2-C_9)$heteroaryl$(C_1-C_6)$alkoxy-, $(C_6-C_{10})$aryl$(C_1-C_6)$alkythio-, $(C_2-C_9)$heteroaryl$(C_1-C_6)$alkythio-, hydroxy$(C_1-C_6)$alkyl-, $(C_6-C_{10})$aryl$(C_1-C_6)$alkyl-, $(C_2-C_9)$heteroaryl$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylamino$(C_1-C_6)$alkyl-, $((C_1-C_6)$alkyl$)_2$amino$(C_1-C_6)$alkyl-, $[(C_6-C_{10})$aryl$(C_1-C_6)$alkyl]amino$(C_1-C_6)$alkyl-, $[(C_6-C_{10})$aryl$(C_1-C_6)$alkyl]$((C_1-C_6)$alkyl)amino$(C_1-C_6)$alkyl-, $(C_6-C_{10})$aryl, $[(C_2-C_9)$heteroaryl$(C_1-C_6)$alkyl]amino$(C_1-C_6)$alkyl-, $(C_2-C_9)$heteroaryl and $[(C_2-C_9)$heteroaryl$(C_1-C_6)$alkyl]$((C_1-C_6)$alkyl)amino$(C_1-C_6)$alkyl-; wherein each of said $(C_6-C_{10})$aryl or $(C_2-C_9)$heteroaryl moieties of said $(C_6-C_{10})$aryl$(C_1-C_6)$alkoxy-, $(C_2-C_9)$heteroaryl$(C_1-C_6)$alkoxy-, $(C_6-C_{10})$aryl$(C_1-C_6)$alkythio-, $(C_2-C_9)$heteroaryl$(C_1-C_6)$alkythio-, $(C_6-C_{10})$aryl$(C_1-C_6)$alkyl-, $(C_2-C_9)$heteroaryl$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $[(C_6-C_{10})$aryl$(C_1-C_6)$alkyl]amino$(C_1-C_6)$alkyl-, $[(C_6-C_{10})$aryl$(C_1-C_6)$alkyl]$((C_1-C_6)$alkyl)amino $(C_1-C_6)$alkyl-, $(C_6-C_{10})$aryl, $[(C_2-C_9)$heteroaryl $(C_1-C_6)$alkyl]amino$(C_1-C_6)$alkyl-, $(C_2-C_9)$heteroaryl and $[(C_2-C_9)$heteroaryl$(C_1-C_6)$alkyl]$((C_1-C_6)$alkyl) amino$(C_1-C_6)$alkyl- are optionally substituted on any of the ring carbon atoms capable of forming an additional bond by one or more substituents per ring, most preferably one to three substituents on the terminal ring independently selected from fluoro, chloro, cyano, nitro, trifluoromethyl, $(C_1-C_6)$alkoxy, $(C_6-C_{10})$ aryloxy, trifluoromethoxy, difluoromethoxy, or $(C_1-C_6)$ alkyl;

or $R^1$ can be taken together with $R^2$ to form a carbonyl group;

or $R^3$ can be taken together with $R^4$ to form a carbonyl group;

Q is $(C_1-C_6)$alkyl, $(C_6-C_{10})$aryl, $(C_2-C_9)$heteroaryl, $(C_6-C_{10})$aryloxy$(C_1-C_6)$alkyl-, $(C_6-C_{10})$aryloxy $(C_6-C_{10})$aryl-, $(C_6-C_{10})$aryloxy$(C_2-C_9)$heteroaryl-, $(C_6-C_{10})$aryl$(C_1-C_6)$alkyl-, $(C_6-C_{10})$aryl$(C_6-C_{10})$ aryl-, $(C_6-C_{10})$aryl$(C_2-C_9)$heteroaryl-, $(C_6-C_{10})$aryl $(C_6-C_{10})$aryl$(C_1-C_6)$alkyl-, $(C_6-C_{10})$aryl$(C_6-C_{10})$aryl $(C_6-C_{10})$aryl-, $(C_6-C_{10})$aryl$(C_6-C_{10})$aryl$(C_2-C_9)$ heteroaryl-, $(C_2-C_9)$heteroaryl$(C_1-C_6)$alkyl-, $(C_2-C_9)$ heteroaryl$(C_6-C_{10})$aryl, $(C_2-C_9)$heteroaryl$(C_2-C_9)$ heteroaryl-, $(C_6-C_{10})$aryl$(C_1-C_6)$alkoxy$(C_1-C_6)$alkyl-, $(C_6-C_{10})$aryl$(C_1-C_6)$alkoxy$(C_6-C_{10})$aryl-, $(C_6-C_{10})$ aryl$(C_1-C_6)$alkoxy$(C_2-C_9)$heteroaryl-, $(C_2-C_9)$ heteroaryloxy$(C_1-C_6)$alkyl-, $(C_2-C_9)$heteroaryloxy $(C_6-C_{10})$aryl-, $(C_2-C_9)$heteroaryloxy$(C_2-C_9)$ heteroaryl-, $(C_2-C_9)$heteroaryl$(C_1-C_6)$alkoxy$(C_1-C_6)$ alkyl-, $(C_2-C_9)$heteroaryl$(C_1-C_6)$alkoxy$(C_6-C_{10})$aryl- or $(C_2-C_9)$heteroaryl$(C_1-C_6)$alkoxy$(C_2-C_9)$ heteroaryl-;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$ aryloxy$(C_1-C_6)$alkyl-, $(C_6-C_{10})$aryloxy$(C_6-C_{10})$aryl-, $(C_6-C_{10})$aryloxy$(C_2-C_9)$heteroaryl-, $(C_6-C_{10})$aryl $(C_1-C_6)$alkyl, $(C_6-C_{10})$aryl$(C_6-C_{10})$aryl-, $(C_6-C_{10})$ aryl$(C_2-C_9)$heteroaryl-, $(C_6-C_{10})$aryl$(C_6-C_{10})$aryl $(C_1-C_6)$alkyl-, $(C_6-C_{10})$aryl$(C_6-C_{10})$aryl$(C_6-C_{10})$ aryl-, $(C_6-C_{10})$aryl$(C_6-C_{10})$aryl$(C_2-C_9)$heteroaryl-, $(C_2-C_9)$heteroaryl$(C_1-C_6)$alkyl-, $(C_2-C_9)$heteroaryl $(C_6-C_{10})$aryl, $(C_2-C_9)$heteroaryl$(C_2-C_9)$heteroaryl-, $(C_6-C_{10})$aryl$(C_1-C_6)$alkoxy$(C_1-C_6)$alkyl-, $(C_6-C_{10})$ aryl$(C_1-C_6)$alkoxy$(C_6-C_{10})$aryl-, $(C_6-C_{10})$aryl $(C_1-C_6)$alkoxy$(C_2-C_9)$heteroaryl-, $(C_2-C_9)$ heteroaryloxy$(C_1-C_6)$alkyl-, $(C_2-C_9)$heteroaryloxy $(C_6-C_{10})$aryl-, $(C_2-C_9)$heteroaryloxy$(C_2-C_9)$ heteroaryl-, $(C_2-C_9)$heteroaryl$(C_1-C_6)$alkoxy$(C_1-C_6)$ alkyl-, $(C_2-C_9)$heteroaryl$(C_1-C_6)$alkoxy$(C_6-C_{10})$aryl- or $(C_2-C_9)$heteroaryl$(C_1-C_6)$alkoxy$(C_2-C_9)$ heteroaryl- is optionally substituted on any of the ring carbon atoms capable of forming an additional bond by one or more substituents per ring, preferably one to three substituents per ring, most preferably one to three substituents on the terminal ring independently selected from fluoro, chloro, bromo, $(C_1-C_6)$alkyl, $(C_1-C_6)$ alkoxy, perfluoro$(C_1-C_3)$alkyl, perfluoro$(C_1-C_3)$ alkoxy and $(C_6-C_{10})$aryloxy;

with the proviso that when the dotted line is a double bond that one of $R^1$ or $R^2$ and one of $R^3$ or $R^4$ is absent;

with the proviso that when one of $R^1$ or $R^2$ is hydroxy then the other of $R^1$ or $R^2$ cannot be hydroxy, $(C_1-C_6)$ alkoxy, $(C_1-C_6)$alkoxy$(C_1-C_6)$alkoxy-, $((C_1-C_6)$alkyl$)_2$amino$(C_1-C_6)$alkoxy-, $(C_1-C_6)$alkylthio, $(C_6-C_{10})$ aryl$(C_1-C_6)$alkoxy-, $(C_2-C_9)$heteroaryl$(C_1-C_6)$ alkoxy-, $(C_6-C_{10})$aryl$(C_1-C_6)$alkythio-, or $(C_2-C_9)$ heteroaryl$(C_1-C_6)$alkythio-, and with the proviso that when one of $R^3$ or $R^4$ is hydroxy then the other of $R^3$ or $R^4$ cannot be hydroxy, $(C_1-C_6)$ alkoxy, $(C_1-C_6)$alkoxy$(C_1-C_6)$alkoxy-, $((C_1-C_6)$alkyl$)_2$amino$(C_1-C_6)$alkoxy-, $(C_1-C_6)$alkylthio, $(C_6-C_{10})$ aryl$(C_1-C_6)$alkoxy-, $(C_2-C_9)$heteroaryl$(C_1-C_6)$ alkoxy-, $(C_6-C_{10})$aryl$(C_1-C_6)$alkythio-, or $(C_2-C_9)$ heteroaryl$(C_1-C_6)$alkythio-, or a pharmaceutically acceptable salt thereof.

2. A compound according to claim 1, wherein Q is optionally substituted $(C_6-C_{10})$aryl, $(C_6-C_{10})$aryl$(C_6-C_{10})$ aryl-, $(C_6-C_{10})$aryloxy$(C_6-C_{10})$aryl-, $(C_6-C_{10})$aryloxy $(C_2-C_9)$heteroaryl-, $(C_2-C_9)$heteroaryl-, $(C_2-C_9)$heteroaryl $(C_2-C_9)$heteroaryl-, $(C_6-C_{10})$aryl$(C_2-C_9)$heteroaryl-, $(C_2-C_9)$heteroaryl$(C_6-C_{10})$aryl-, $(C_2-C_9)$heteroaryloxy $(C_6-C_{10})$aryl-, $(C_6-C_{10})$aryl$(C_1-C_6)$alkoxy$(C_6-C_{10})$-aryl-, or $(C_2-C_9)$heteroaryl$(C_1-C_6)$alkoxy$(C_6-C_{10})$aryl-.

3. A compound according to claim 1, wherein Q is optionally substituted $(C_6-C_{10})$aryloxy$(C_6-C_{10})$aryl- or $(C_6-C_{10})$aryl$(C_1-C_6)$alkoxy$(C_6-C_{10})$aryl-.

4. A compound according to claim 3, wherein the $(C_6-C_{10})$aryloxy ring of said $(C_6-C_{10})$aryloxy$(C_6-C_{10})$aryl- group is optionally mono-substituted in the 4-position of the ring.

5. A compound according to claim 1, wherein $R^1$ or $R^2$ is $(C_1-C_6)$alkyl, hydroxy$(C_1-C_6)$alkyl-, $(C_6-C_{10})$aryl$(C_1-C_6)$alkyl-, $(C_2-C_9)$heteroaryl$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylamino$(C_1-C_6)$alkyl-, $((C_1-C_6)$alkyl$)_2$amino$(C_1-C_6)$alkyl-, $[(C_6-C_{10})$aryl$(C_1-C_6)$alkyl]amino$(C_1-C_6)$alkyl-, $[(C_6-C_{10})$aryl$(C_1-C_6)$alkyl]((C_1-C_6)$alkyl)amino$(C_1-C_9)$alkyl-, $(C_6-C_{10})$aryl, $[(C_2-C_9)$heteroaryl$(C_1-C_6)$alkyl]amino$(C_1-C_6)$alkyl-, $(C_2-C_9)$heteroaryl, or $[(C_2-C_9)$heteroaryl$(C_1-C_6)$alkyl]((C_1-C_6)$alkyl)amino$(C_1-C_6)$alkyl-.

6. A compound according to claim 1, wherein $R^1$ or $R^2$ is $(C_1-C_6)$alkyl, hydroxy$(C_1-C_6)$alkyl-, $(C_6-C_{10})$aryl$(C_1-C_6)$alkyl-, $(C_2-C_9)$heteroaryl$(C_1-C_6)$alkyl- $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_6-C_{10})$aryl or $(C_2-C_9)$heteroaryl.

7. A compound according to claim 1, wherein $R^1$ or $R^2$ is $(C_1-C_6)$alkyl, $(C_6-C_{10})$aryl$(C_1-C_6)$alkyl-, $(C_2-C_9)$heteroaryl$(C_1-C_6)$alkyl-, $(C_6-C_{10})$aryl or $(C_2-C_9)$heteroaryl.

8. A compound according to claim 1, wherein $R^1$ or $R^2$ is $(C_1-C_6)$alkyl, $(C_6-C_{10})$aryl or $(C_2-C_9)$heteroaryl.

9. A compound according to claim 1, wherein $R^1$ or $R^2$ is hydroxy$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, or $(C_2-C_9)$heteroaryl$(C_1-C_6)$alkoxy$(C_1-C_6)$alkyl-.

10. A compound according to claim 1, wherein $R^1$ or $R^2$ is $(C_1-C_6)$alkoxy$(C_1-C_6)$alkyl.

11. A compound according to claim 1, wherein $R^1$ or $R^2$ is $(C_1-C_6)$alkoxy, $(C_1-C_6)$alkoxy$(C_1-C_6)$alkoxy-, $((C_1-C_6)$alkyl$)_2$amino$(C_1-C_6)$alkoxy-, $(C_1-C_6)$alkylthio, $(C_6-C_{10})$aryl$(C_1-C_6)$alkoxy-, $(C_2-C_9)$heteroaryl$(C_1-C_6)$alkoxy-, $(C_6-C_{10})$aryl$(C_1-C_6)$alkythio-, or $(C_2-C_9)$heteroaryl$(C_1-C_6)$alkythio-.

12. A compound according to claim 1, wherein $R^1$ or $R^2$ is $(C_1-C_6)$alkoxy, $(C_1-C_6)$alkoxy$(C_1-C_6)$alkoxy-, $(C_6-C_{10})$aryl$(C_1-C_6)$alkoxy-, or $(C_2-C_9)$heteroaryl$(C_1-C_6)$alkoxy-.

13. A compound according to claim 1, wherein $R^1$ or $R^2$ is $(C_1-C_6)$alkoxy or $(C_1-C_6)$alkoxy$(C_1-C_6)$alkoxy-.

14. A compound according to claim 1, wherein $R^3$ or $R^4$ is $(C_1-C_6)$alkyl, hydroxy$(C_1-C_6)$alkyl-, $(C_6-C_{10})$aryl$(C_1-C_6)$alkyl-, $(C_2-C_9)$heteroaryl$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylamino$(C_1-C_6)$alkyl-, $((C_1-C_6)$alkyl$)_2$amino$(C_1-C_6)$alkyl-, $[(C_6-C_{10})$aryl$(C_1-C_6)$alkyl]amino$(C_1-C_6)$alkyl-, $[(C_6-C_{10})$aryl$(C_1-C_6)$alkyl]((C_1-C_6)$alkyl)amino$(C_1-C_6)$alkyl-, $(C_6-C_{10})$aryl, $[(C_2-C_9)$heteroaryl $(C_1-C_6)$alkyl]amino$(C_1-C_6)$alkyl-, $(C_2-C_9)$heteroaryl, or $[(C_2-C_9)$heteroaryl$(C_1-C_6)$alkyl]((C_1-C_6)$alkyl)amino$(C_1-C_6)$alkyl-.

15. A compound according to claim 1, wherein $R^3$ or $R^4$ is $(C_1-C_6)$alkyl, hydroxy$(C_1-C_6)$alkyl-, $(C_6-C_{10})$aryl$(C_1-C_6)$alkyl-, $(C_2-C_9)$heteroaryl$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_6-C_{10})$aryl or $(C_2-C_9)$heteroaryl.

16. A compound according to claim 1, wherein $R^3$ or $R^4$ is $(C_1-C_6)$alkyl, $(C_6-C_{10})$aryl$(C_1-C_6)$alkyl-, $(C_2-C_9)$heteroaryl$(C_1-C_6)$alkyl-, $(C_6-C_{10})$aryl or $(C_2-C_9)$heteroaryl.

17. A compound according to claim 1, wherein $R^3$ or $R^4$ is $(C_1-C_6)$alkyl, $(C_6-C_{10})$aryl or $(C_2-C_9)$heteroaryl.

18. A compound according to claim 1, wherein $R^3$ or $R^4$ is hydroxy$(C_1-C_6)$alkyl-, $(C_1-C_6)$alkoxy$(C_1-C_6)$alkyl-, $(C_6-C_{10})$aryl$(C_1-C_6)$alkoxy$(C_1-C_6)$alkyl-, or $(C_2-C_9)$heteroaryl$(C_1-C_6)$alkoxy$(C_1-C_6)$alkyl-.

19. A compound according to claim 1, wherein $R^3$ or $R^4$ is $(C_1-C_6)$alkoxy$(C_1-C_6)$alkyl.

20. A compound according to claim 1, wherein $R^3$ or $R^4$ is $(C_1-C_6)$alkoxy, $(C_1-C_6)$alkoxy$(C_1-C_6)$alkoxy-, $((C_1-C_6)$alkyl$)_2$amino$(C_1-C_6)$alkoxy-, $(C_1-C_6)$alkylthio, $(C_6-C_{10})$aryl$(C_1-C_6)$alkoxy-, $(C_2-C_9)$heteroaryl$(C_1-C_6)$alkoxy-, $(C_6-C_{10})$aryl$(C_1-C_6)$alkythio-, or $(C_2-C_9)$heteroaryl $(C_1-C_6)$alkythio-.

21. A compound according to claim 1, wherein $R^3$ or $R^4$ is $(C_1-C_6)$alkoxy, $(C_1-C_6)$alkoxy$(C_1-C_6)$alkoxy-, $(C_6-C_{10})$aryl$(C_1-C_6)$alkoxy-, or $(C_2-C_9)$heteroaryl$(C_1-C_6)$alkoxy-.

22. A compound according to claim 1, wherein $R^3$ or $R^4$ is $(C_1-C_6)$alkoxy or $(C_1-C_6)$alkoxy$(C_1-C_6)$alkoxy.

23. A compound according to claim 1, wherein $R^3$ is hydroxy and $R^4$ is $(C_1-C_6)$alkyl.

24. A compound according to claim 1, wherein said compound is selected from the racemate or either the R or S isomer of the group consisting of:

3-[4-(4-fluorophenoxy)benzenesulfonylamino] tetrahydropyran-3-carboxylic acid hydroxyamide and 3-[4-(4-chlorophenoxy)benzenesulfonylamino] tetrahydropyran-3-carboxylic acid hydroxyamide.

25. A pharmaceutical composition for the treatment of a condition selected from the group consisting of arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of claim 1 effective in such treatment and a pharmaceutically acceptable carrier.

26. A method for treating a condition selected from the group consisting of arthritis, inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm (including abdominal aortic aneurysm and brain aortic aneurysm), congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of claim 1, effective in treating such a condition.

27. A pharmaceutical composition for the treatment of a condition which can be treated by the inhibition of matrix metalloproteinases in a mammal, including a human, comprising an amount of a compound of claim 1 effective in such treatment and a pharmaceutically acceptable carrier.

28. A pharmaceutical composition for the treatment of a condition which can be treated by the inhibition of a mammalian reprolysin in a mammal, including a human, comprising an amount of a compound of claim 1 effective in such treatment and a pharmaceutically acceptable carrier.

29. A method for the inhibition of matrix metalloproteinases in a mammal, including a human, comprising administering to said mammal an effective amount of a compound of claim 1.

30. A method for the inhibition of a mammalian reprolysin in a mammal, including a human, comprising administering to said mammal an effective amount of a compound of claim 1.

* * * * *